(12) United States Patent
Taghibiglou

(10) Patent No.: US 10,859,581 B2
(45) Date of Patent: Dec. 8, 2020

(54) METHODS AND KITS FOR DETECTING BRAIN INJURY

(71) Applicant: University of Saskatchewan, Saskatoon (CA)

(72) Inventor: Changiz Taghibiglou, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 75 days.

(21) Appl. No.: 15/319,436

(22) PCT Filed: Jun. 12, 2015

(86) PCT No.: PCT/CA2015/000416
§ 371 (c)(1),
(2) Date: Dec. 16, 2016

(87) PCT Pub. No.: WO2015/192222
PCT Pub. Date: Dec. 23, 2015

(65) Prior Publication Data
US 2017/0153252 A1    Jun. 1, 2017

Related U.S. Application Data

(60) Provisional application No. 62/013,237, filed on Jun. 17, 2014.

(51) Int. Cl.
| | |
|---|---|
| *G01N 33/68* | (2006.01) |
| *A61K 39/395* | (2006.01) |
| *C07K 14/47* | (2006.01) |
| *A61K 39/00* | (2006.01) |
| *A61B 5/15* | (2006.01) |

(52) U.S. Cl.
CPC ..... *G01N 33/6896* (2013.01); *A61K 39/0007* (2013.01); *C07K 14/47* (2013.01); *G01N 33/6893* (2013.01); *A61B 5/15003* (2013.01); *A61B 5/150022* (2013.01); *G01N 2333/47* (2013.01); *G01N 2333/70596* (2013.01); *G01N 2800/28* (2013.01); *G01N 2800/2828* (2013.01); *G01N 2800/40* (2013.01); *G01N 2800/56* (2013.01)

(58) Field of Classification Search
CPC .... G01N 33/6896; G01N 33/53; G01N 33/58; G01N 33/68; A61K 39/0007
See application file for complete search history.

(56) References Cited

FOREIGN PATENT DOCUMENTS

| WO | 2007/136617 A2 | 11/2007 |
|---|---|---|
| WO | 2013/090285 A1 | 6/2013 |

OTHER PUBLICATIONS

Yarnell, A.M. et al, "Blast Traumatic Brain Injury in the Rat Using a Blast Overpressure Model", Current Protocols in Neuroscience, Jan. 2013, Supplement 62, pp. 9.41.1-9.41.14.
"Enzyme Immunoassay Kit for the Determination of PrPc", SPI Bio, Oct. 2004, Catalogue A05201, pp. 1-9.
Zahn, Ralph, "The Octapeptide Repeats in Mammalian Prion Protein Constitute a pH-dependent Folding and Aggregation Site", Journal of Molecular Biology, Dec. 2003, vol. 334, pp. 477-488.
Pham, N. et al., "Plasma Soluble Prion Protein, a Potential Biomarker for Sport-Related Concussions: A Pilot Study", PLoS One, Feb. 2, 2015, vol. 10(2): e0117286, pp. 1-12.
Pham, N. et al., "Primary Blast-induced Traumatic Brain Injury in Rats Leads to Increased Prion Protein in Plasma: A Potential Biomarker for Blast-Induced Traumatic Brain Injury", Journal of Neurotrauma, Jan. 1, 2015, vol. 32, pp. 58-65.
Weise, J. et al., "Upregulation of cellular prion protein (PrPc) after focal cerebral ischemia and influence of lesion severity", Neuroscience Letters, 2004, vol. 372, pp. 146-150.
Roucou, X. and Leblanc, A.C., "Cellular prion protein neuroprotective function: implications in prion diseases", Journal of Molecular Medicine, 2005, vol. 83, pp. 3-11.
McLellan, N.F. et al., "Prion Protein Accumulation and Neuroprotection in Hypoxic Brain Damage", The American Journal of Pathology, Jul. 2004, vol. 165, No. 1, pp. 227-235.
Weise, J. et al., "Deletion of Cellular Prion Protein Results in Reduced Akt Activation, Enhanced Postischemic Caspase-3 Activation, and Exacerbation of Ischemic Brain Injury", Stroke, 2006, vol. 37, pp. 1296-1300.
Sawyer, T.W. et al., "High-Fidelity Simulation of Primary Blast: Direct Effects on the Head", J Neurotrauma, Jul. 1, 2016, vol. 33, pp. 1181-1193.
Rubenstein, R. et al., "Tau phosphorylation induced by severe closed head traumatic brain injury is linked to the cellular prion protein", Acta Neuropathol Commun, 2017; 5:30, pp. 1-17.
Posti, J.P. et al., "Glial Fibrillary Acidic Protein and Ubiquitin C-Terminal Hydrolase-L1 Are Not Specific Biomarkers for Mild CT-Negative Traumatic Brain Injury", J Neurotrauma, Apr. 1, 2017, vol. 34, pp. 1427-1438.
Prion Protein (PrPc) ELISA: Enzyme immunoassay for the determination of native Prion Protein (PrPc) in brain extracts. [Pamphlet]. (2004). Germany, Hamburg: IBL International GmbH. Pamphalet from SPI Bio France.
Material Safety Data Sheet [Pamphlet]. (2011). Switzerland, Prionatis Ag, The Prion Company.

*Primary Examiner* — Robert C Hayes

(74) *Attorney, Agent, or Firm* — Bereskin & Parr LLP/S.E.N.C.R.L., s.r.l.; Ainslie Parsons; Melanie Szweras

(57) ABSTRACT

The disclosure provides methods of detecting and monitoring brain injury in a test subject comprising analyzing a blood sample from the test subject for increased levels of $PrP^C$. The disclosure also provides kits for measuring the amount of $PrP^C$ in a blood sample.

10 Claims, 12 Drawing Sheets
Specification includes a Sequence Listing.

A

B

A

B

SEQUENCE LISTING

```
<160> NUMBER OF SEQ ID NOS: 2

<210> SEQ ID NO 1
<211> LENGTH: 10
<212> TYPE: PRT
<213> ORGANISM: Homo sapiens

<400> SEQUENCE: 1

Asp Tyr Glu Asp Arg Tyr Tyr Arg Glu Asn
1               5                   10

<210> SEQ ID NO 2
<211> LENGTH: 41
<212> TYPE: PRT
<213> ORGANISM: Homo sapiens

<400> SEQUENCE: 2

Pro Gln Gly Gly Gly Gly Trp Gly Gln Pro His Gly Gly Gly Trp Gly
1               5                   10                  15

Gln Pro His Gly Gly Gly Trp Gly Gln Pro His Gly Gly Gly Trp Gly
            20                  25                  30

Gln Pro His Gly Gly Gly Trp Gly Gln
        35                  40
```

METHODS AND KITS FOR DETECTING BRAIN INJURY

RELATED APPLICATIONS

This application is a national phase entry of PCT/CA2015/000416 filed Jun. 12, 2015 (which designates the U.S.) which claims the benefit of priority to U.S. Provisional application No. 62/013,237 filed Jun. 17, 2014, the contents of both of which are incorporated herein by reference in their entirety.

INCORPORATION OF SEQUENCE LISTING

A computer readable form of the Sequence Listing "13764-P43934US02_SequenceListing.txt" (4,096 bytes), submitted via EFS-WEB and created Dec. 16, 2016, is herein incorporated by reference.

FIELD

The disclosure relates to methods and kits for analyzing blood to detect a biomarker for brain injury.

BACKGROUND

More than any past wars, traumatic brain injury (TBI) has been a prevalent issue for coalition forces serving in the wars in Afghanistan and Iraq. It is estimated that 15-28% of returning veterans have sustained a TBI through these conflicts (Okie 2005; Hoge et al., 2008). TBI is associated with long-term disabilities and psychiatric diseases and is often described as the 'signature injury' of these wars (Alvarez 2008; Tanielian and Jaycox, 2008), largely as a result of increased survival rates of service members thanks to advances in medical interventions and protective equipment (Regan 2004; Warden 2006). There are various causes for TBI, with 68% of military cases reported due to blast exposure (Hoge et al., 2008). Blast exposure can be a consequence of standard military ordinances, grenades, landmines or, as prominently seen throughout the recent wars, from attacks using improvised explosive devices (IEDs), accounting for about 40% of coalition deaths and a similar number of TBI cases in Iraq (Brookings Institution 2008). Worldwide estimates of terrorist attacks in both warzones and civilian settings increased four-fold from 1999-2006, with related injuries increasing eight-fold (Wolf et al., 2009). The common characteristic of IEDs is the immense wave of blast overpressure produced. At the point of detonation, there is an instantaneous expansion of gas, producing a blast wave outwards faster than the speed of sound, accompanied by a blast wind that can reach speeds over several hundred km/h (Elder et al., 2010; Wolf et al., 2009).

The underlying mechanisms of how blast waves affect the brain are not fully understood. Animal studies have established that the blast wave is transmitted through the skull to the brain (Bauman et al., 2009; Chavko et al., 2007). Schardin described explosive inertial (shearing) forces in which tissues of varying densities move at different speeds in response to a blast; thus, as the wave passes through an organ, structural components of different densities can be tethered and damaged by this shearing force (Schardin 1950; Wolf et al., 2009). Furthermore, closed-space explosions, such as within or surrounding buildings, result in higher injury severity and mortality when compared in open-space due to the increased magnitude and duration by reflected blast waves off multiple surfaces (Leibovici et al., 1996). Thus, there is a strong likelihood that those sustaining TBI in Afghanistan and Iraq have experienced such shearing forces in the brain.

Traumatic brain injury (TBI) is also the leading cause of death in North America for individuals between the ages of 1 to 45. U.S. estimates from the Center for Disease Control report 1.7 million cases of TBI annually, contributing to a third of all injury-related deaths (CDC 2012). Patients suffering from head trauma are managed according to standardized guidelines based on their Glasgow Coma Scale (GCS). Computerized tomography (CT) scan is the imaging method of choice in head trauma and is able to detect brain hematomas and skull fractures. Current guidelines recommend head CT scan in all patients with GCS 14 or less. Patients are treated based on their neurologic status and findings on their CT scan. Large epidural hematomas (>30 ml in volume) and subdural hematomas >10 mm in thickness or associated with more than 5 mm in midline shift should be surgically evacuated. Patients with epidural hematomas and GCS score ≤8 who have pupillary abnormalities and patients with subdural hematomas who have GCS score 58 or whose GCS scored has decreased by ≥2 points from the time of admission are also candidates for surgery. Evacuation of intracranial hemorrhage is recommended if it is in the posterior fossa. Open skull fractures and depressed skull fractures, with displacement more than the thickness of the cranium, are also treated surgically. A course of prophylactic anti-epileptic treatment is recommended in all patients with brain hematomas for 7 days.

Concussion is a complex pathophysiological process and is considered as a subset of mild traumatic brain injury (mTBI). It causes a transient disturbance of brain function resulting in less severe brain injury. Concussions are the consequence of a direct or indirect blow that results in a sudden angular acceleration or deceleration of the brain tissue within the calvarium. In the United States alone, 3.8 million cases of sport-related concussions occur annually and high-contact sports such as American football, hockey, rugby, soccer, and basketball have among the highest incidence of concussion (Daneshvar et al., 2011; Harmon et al., 2013; Langlois et al., 2006; Meehan et al., 2011). Considering unreported cases, it is highly likely that the incidence of sport-related concussions is even higher (Meehan et al., 2013).

Clinical manifestations of sport-related concussions may include a variety of symptoms such as loss of consciousness, headache, dizziness, amnesia, nausea, confusion, fatigue, sleep disturbances, balance and memory impairment, slurred speech, and light sensitivity. At the molecular pathophysiological levels, most of these symptoms are direct or indirect results of significant alterations in ionic balance, neurotransmitter activation, axonal integrity, and energy metabolism in the CNS (Barkhourdarian et al., 2011; McKee et al., 2014).

Although most sport-related concussions are benign and athletes typically will fully recover if they get adequate rest, multiple concussions in a short period of time may lead to devastating long-term sequelae and prolonged functional impairment, including post-concussive syndrome, neurodegenerative diseases, chronic traumatic encephalopathy, as well as rare catastrophic consequences called second impact syndrome (Boden et al., 2007; Gavett et al., 2011; Halstead et al., 2010). Second impact syndrome is a post-concussion cerebral edema, which results in coma and severe neurological deficits and is often deadly. Thus, it is absolutely essential to manage concussions properly and to avoid repetitive concussive events in those who have already experienced mTBI. Since most mTBI cases show no abnormalities on computed tomography (CT) and conventional magnetic resonance imaging (MRI), identifying those athletes affected by concussion remains a challenging issue for coaches and sport medicine specialists (Belanger et al., 2007). A promising approach to ease these challenges has focused on the detection of protein biomarkers of sport-related concussion. Protein biomarkers are readily accessible in biological fluids such as plasma and serum, which may serve as valuable tools in identifying concussive athletes at greater risk for deterioration and in the guidance of immediate post-concussion therapeutic interventions as well as decision making on return to play. Several potential protein biomarkers have been identified for TBI, of which a few have been tested in sport related concussion (reviewed in Forde et al., 2014; Guingab-Cagmat et al., 2013; Jeter et al., 2013; Strathmann et al., 2014; Wolf et al., 2013; Yokobori et al., 2013; Zetterberg et al., 2013). Among these potential protein biomarkers, S100B, cleaved tau (C-tau), glial fibrillary acidic protein (GFAP), neuron-specific enolase (NSE), Myelin-basic protein (MBP), Ubiquitin C-terminal hydrolase-L1(UCH-L1), αII-spectrin breakdown products (SBDPs), Interleukin-6 (IL-6) and tumor necrosis factor-alpha (TNF-α) have been more widely studied (reviewed in Yokobori et al., 2013; Zetterberg et al., 2013).

SUMMARY

The present inventor describes a novel method for quantifying prion proteins to detect brain injury associated with increased cellular prion protein ($PrP^C$).

Accordingly, the disclosure provides a method of detecting brain injury in a test subject comprising (a) contacting a blood sample from the test subject with a probe that binds to $PrP^C$, and (b) detecting and/or quantifying the amount of $PrP^C$, wherein a difference or similarity in the amount of $PrP^C$ compared to a control is indicative of the test subject having suffered a brain injury.

In one embodiment, the control is representative of the amount of $PrP^C$ from a blood sample of a subject without brain injury, such as a cut-off value obtained from historical data, and an increased amount of $PrP^C$ to the control is indicative of the subject having a brain injury. In another embodiment, the control is representative of the amount of $PrP^C$ from a blood sample of a subject having a brain injury and a similar or greater amount of $PrP^C$ to the control is indicative of the test subject having a brain injury.

In yet another embodiment, the control is representative of the amount of $PrP^C$ from a blood sample of a subject that is an athlete during off-season and an increased amount of $PrP^C$ to the control is indicative of the subject having a brain injury. In a further embodiment, the control is representative of the amount of $PrP^C$ from a blood sample of a subject that recently had a sports-related concussion and a similar or greater amount of $PrP^C$ to the control is indicative of the test subject having a brain injury.

In another embodiment, the control is a reference baseline level of $PrP^C$ of the same test subject. In yet another embodiment, the control is an average reference baseline level of the general population. In a further embodiment, the control is an average reference baseline level of athletes taken during the off-season. In yet another embodiment, the control is an average reference baseline for a subject of the same age. In an embodiment, the subject is a child and the control is an average reference baseline level of the child population.

In one embodiment, the method further comprises obtaining a blood sample from the subject prior to contacting the blood sample with the probe. In one embodiment, the sample is obtained or was obtained 1 to 6 days after a suspected brain injury or injury event.

In another embodiment, there is provided a method of monitoring a subject having a brain injury comprising:
  (i) (a) contacting a blood sample from the subject obtained at a first time point with a probe that binds to $PrP^C$;
  (b) detecting and/or quantifying the amount of $PrP^C$ at the first time point;
  (ii) (a) contacting a blood sample from the subject obtained at a second time point with a probe that binds to $PrP^C$;
  (b) detecting and/or quantifying the amount of $PrP^C$ at the second time point; and
  (iii) comparing the amount of $PrP^C$ from the first time point with the amount of $PrP^C$ from the second time point; wherein an increase in the amount of $PrP^C$ indicates an increase in the severity of the brain injury and wherein a decrease in the amount of $PrP^C$ indicates an improvement in the brain injury.

In one embodiment, the method further comprises obtaining the blood sample from the subject at the first time point and/or the second time point prior to contacting the blood sample with the probe.

In yet another embodiment, there is provided a method of determining whether a subject has suffered a brain injury due to an injury event comprising:
  (i) (a) contacting a blood sample from the subject obtained at a first time point prior to the injury event with a probe that binds to $PrP^C$;
  (b) detecting and/or quantifying the amount of $PrP^C$ at the first time point;
  (ii) (a) contacting a blood sample from the subject obtained at a second time point after the injury event with a probe that binds to $PrP^C$;
  (b) detecting and/or quantifying the amount of $PrP^C$ at the second time point; and
  (iii) comparing the amount of $PrP^C$ from the first time point with the amount of $PrP^C$ from the second time point; wherein an increase in the amount of $PrP^C$ indicates that the subject has suffered a brain injury due to the injury event.

In one embodiment, the method further comprises obtaining the blood sample from the subject prior to contacting the blood sample with the probe in (i)(a) and/or (ii)(a).

In another embodiment, the first time point provides a baseline level of the subject, such as a pre-combat level of a subject that may be exposed to combat, or an off-season level of a subject that is an athlete that may be prone to a head injury, and the second time point is following the injury event, optionally, 1-6 days after the injury event, such as an explosion, transportation accident or head injury due to a fall or sports-related event.

In another embodiment, there is provided a method of determining whether a subject has suffered a brain injury due to an injury event comprising:
  (i) (a) contacting a blood sample from a subject after the injury event, optionally obtained 1-6 days after, with a probe that binds to $PrP^C$;
  (b) detecting and/or quantifying the amount of $PrP^C$ in (a); and
  (iii) comparing the amount of $PrP^C$ in (b) with a baseline level of the subject; wherein an increase in the amount of $PrP^C$ from the baseline level indicates that the subject has suffered a brain injury due to the injury event.

In one embodiment, the baseline level of the subject is a pre-combat level of a subject that may be exposed to combat, or an off-season level of a subject that is an athlete that may be prone to a head injury.

In an embodiment, the probe is an antibody or antibody fragment that binds to $PrP^C$. In one embodiment, the probe comprises a marker or label for detection, such as a radioactive, fluorescent, biological or enzymatic label. In an alternative embodiment, a secondary binding ligand is used, such as a second antibody or biotin/avidin ligand binding agent, as is known in the art for detection of the probe.

In some embodiments, the amount of $PrP^C$ is quantified, for example, by fluorescence, radioactivity or spectrophotometry depending on the label or marker used. In an embodiment, the amount of $PrP^C$ is quantified by a radioimmunoassay, an enzyme-linked immunoassay, a competitive binding enzyme-linked immunoassay, dot blot, or Western blot, or other assays known in the art. In another embodiment, a suitable detection technology such as a complementary metal-oxide-semiconductor (CMOS) or charge coupled device (CCD) is used and a unique wavelength of light is applied for illumination of the signal. In some embodiments, the method further comprises testing a series of known reference standards, such as serially diluted samples containing known amounts of $PrP^C$, optionally at the same time, wherein the amount of $PrP^C$ in the test subject sample or control sample is quantified by comparing to said reference standards.

In one embodiment, the probe is in solution. In another embodiment, the probe is immobilized on a solid support or support pad, such as filter paper, a multiwell plate or a microchip.

In an embodiment of the method, contacting the blood sample from the subject in (a) with a probe comprises (a.1) contacting the sample with a first probe that binds to $PrP^C$ at a first position; and (a.2) contacting the $PrP^C$ bound to the first probe with a second probe that binds to $PrP^C$ at a second position; wherein either the first or the second probe is detectable.

In an embodiment, the first probe is an antibody or fragment thereof that specifically binds to $PrP^C$ and is immobilized on a solid support and the second probe is an antibody or fragment thereof that specifically binds to $PrP^C$ at a different epitope than the first probe, is detectable and is in solution. In an alternate embodiment, the first probe is an antibody or fragment thereof that specifically binds to $PrP^C$, is detectable and is in solution and the second probe is an antibody or fragment thereof that specifically binds to $PrP^C$ at a different epitope than the first probe and is immobilized on a solid support. In such embodiments, a double antibody-sandwich technique is applied and (b) the amount of $PrP^C$ in the test subject sample is quantified by comparing to reference standards, which may be tested at the same time.

In one embodiment, the detectable probe comprises an enzyme and enzymatic activity can be used to detect and quantify the amount of $PrP^C$ in the sample and in the reference standards. For example, in an embodiment, the detectable probe comprises acetylcholinesterase conjugated to the antibody or antibody fragment. In such an embodiment, Ellman's reagent is mixed with the sample to produce a yellow colour which is indicative of the amount of activity of the enzyme, which can be measured by spectrophotometry at an absorbance of 405 nm.

The disclosure also relates to a kit for analyzing a blood sample to detect brain injury comprising:

(a) a probe that detects the amount of $PrP^C$ in the blood; and (b) instructions for use in detecting brain injury.

In an embodiment, the probe is an antibody or antibody fragment that binds to $PrP^C$. In one embodiment, the probe comprises a marker or label for detection, such as a radioactive, fluorescent, biological or enzymatic label. In an alternative embodiment, a secondary binding ligand is used, such as a second antibody or biotin/avidin ligand binding agent, as is known in the art for detection of the probe.

In some embodiments, the amount of $PrP^C$ is quantified, for example, by fluorescence, radioactivity or spectrophotometry depending on the label or marker used and the kit comprises reagents for such detection. In an embodiment, the amount of $PrP^C$ is quantified by a radioimmunoassay, an enzyme-linked immunoassay, a competitive binding enzyme-linked immunoassay, dot blot, or Western blot, or other assays known in the art and the kit comprises reagents for such assays. In another embodiment, a suitable detection technology such as a complementary metal-oxide-semiconductor (CMOS) or charge coupled device (CCD) is provided with the kit or instructions for such use and a unique wavelength of light is applied for illumination of the signal.

In one embodiment, the probe is in solution. In another embodiment, the probe is immobilized on a solid support or support pad, such as filter paper, a multiwell plate or a microchip.

In another embodiment, the disclosure provides a kit for analyzing a blood sample to detect brain injury comprising:

(a) an immobilized probe that binds to $PrP^C$ at a first position;

(b) a detectable probe that detects $PrP^C$ at a second position; and (c) instructions for use in detecting brain injury.

In an embodiment, the immobilized probe is an antibody or antibody fragment that specifically binds to $PrP^C$ and the detectable probe is an antibody or antibody fragment in solution that specifically binds to $PrP^C$ at a different epitope than the immobilized probe.

In one embodiment, the kit further comprises serially diluted samples of $PrP^C$ to be used as standards for quantifying the amount of $PrP^C$ and optionally, the instructions provided include a step of testing the serially diluted samples optionally at the same time as the test sample.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which.

DETAILED DESCRIPTION

Figure 1:
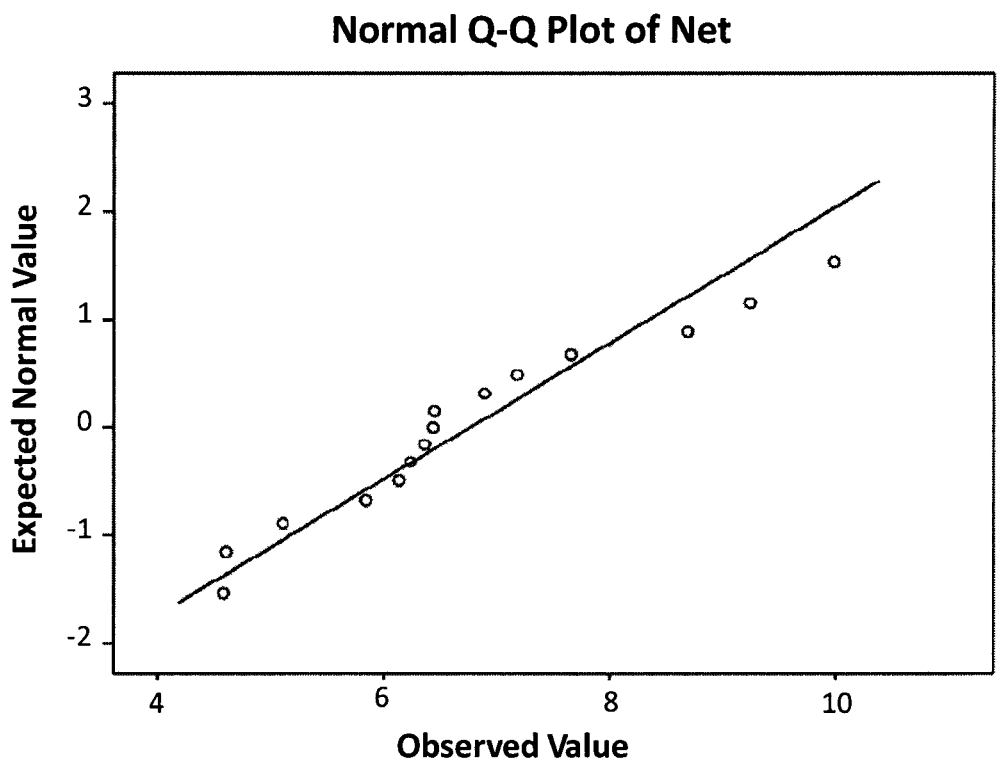
FIG. 1 shows Q-Q plot graph to test normality of the data. a) Net data—control (n=9) vs. net (n=15), b) Restraint data—control vs. restraint (n=12), c) Whiplash data—control vs. whiplash (n=11); d) Overall three treatment data—control vs. three treatment groups—net, restraint, whiplash (n=38).
Figure 1:
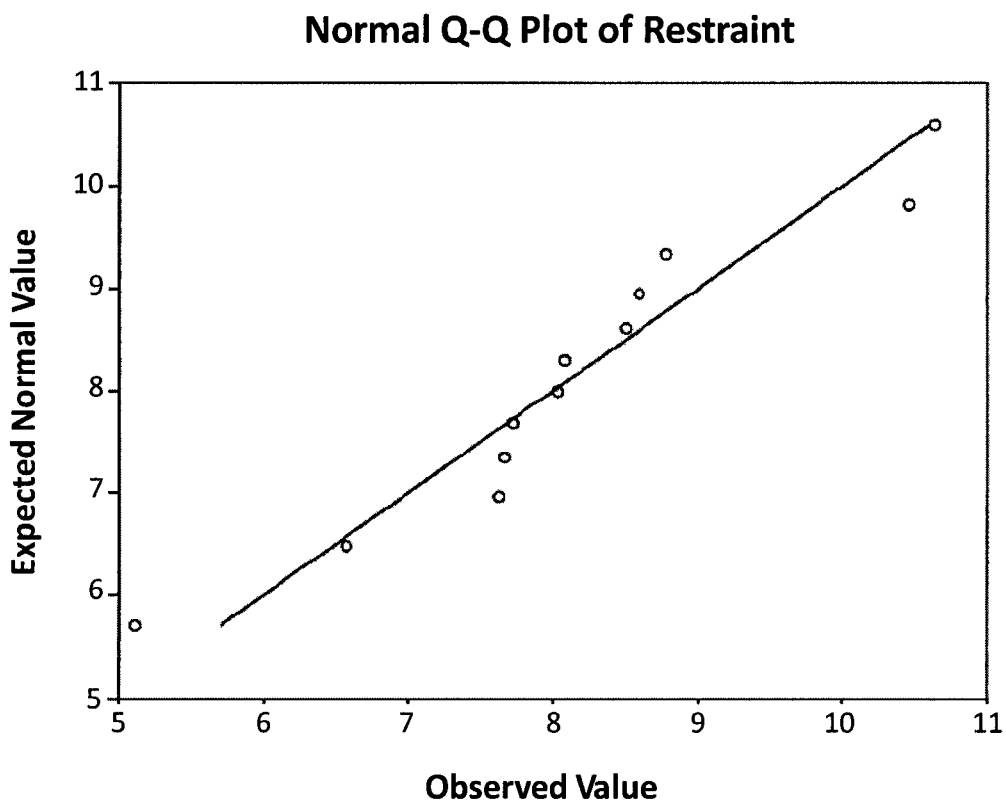
Figure 1:
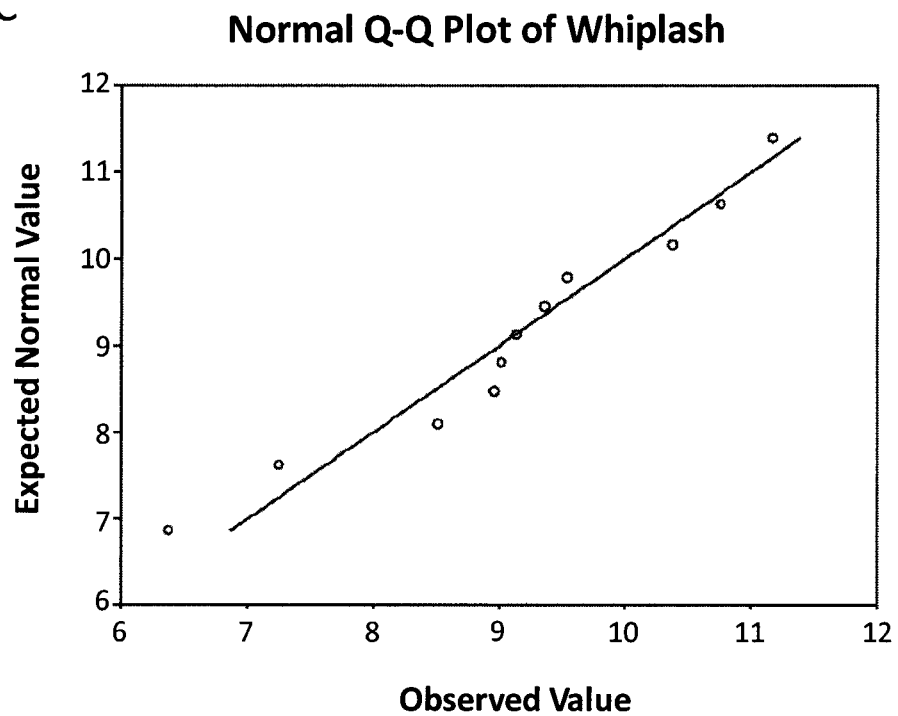

The present inventor has shown an increased amount of $PrP^C$ in the blood of rats subjected to a blast overpressure model, and in particular in the whiplash and restraint treatment groups. Whiplash condition simulates displacement of the head and/or neck due to abrupt acceleration/deceleration forces. Whiplash may be caused by any motion similar to motor vehicle rear-end collisions, amusement park rides, sports injuries, other modes of transportation, falls, or from being hit or violently shaken. Shaken baby syndrome can also result in a whiplash injury (Caffey 1972). The restraint condition simulates victims in a condition that only their heads are exposed to a blast shock wave (mostly military or conflict-zone related TBI), in which there is no significant displacement of the head. The present inventor has also shown an increased amount of $PrP^C$ in the blood of athletes that have suffered a brain injury, i.e. a concussion, compared to non-athletes as well as compared to baseline levels of the same individual.

Accordingly, the disclosure provides a method of detecting brain injury in a test subject comprising (a) contacting a blood sample from the test subject with a probe that binds to $PrP^C$, and (b) detecting and/or quantifying the amount of $PrP^C$, wherein a difference or similarity in the amount of $PrP^C$ compared to a control is indicative of the test subject having suffered a brain injury.

As used herein, the term "$PrP^C$" refers to the cellular form of a prion polypeptide which is a ubiquitously expressed, 208-209 amino acid long, glycophosphatidylinositol (GPI) anchored neuronal lipid raft resident protein, which is highly expressed in neurons. $PrP^C$ may be from any species or source. The Genbank Accession number of human PrP is NG009087. The Genbank Accession number of rat PrP is NM012631 or XM346677.

As used herein, the term "brain injury" refers to an injury to the brain caused by a sudden force or impact, also called "traumatic brain injury", and includes without limitation injuries caused by IEDs, transportation accidents, head banging, excessive shaking, falls and sports-related head injuries, such as concussions. "bTBI" as used herein refers to traumatic brain injury resulting from a blast force. "mTBI" as used herein refers to a minor traumatic brain injury where there is no visible skull wound and generally has no conclusive difference by imaging. Both blast induced and sports related injuries may be minor traumatic brain injuries.

The phrase "detecting a brain injury" also refers to detecting a brain injury in a pre-symptomatic subject. "Detecting a brain injury" also includes detecting the severity of the brain injury.

In one embodiment, the methods described herein include obtaining a blood sample from a subject. Methods of obtaining blood samples are well known in the art.

The methods described herein include the identification of $PrP^C$ in the blood of a subject. The presence of $PrP^C$ can be detected using a number of methods. In one embodiment, $PrP^C$ proteins are detected using probes that specifically bind to and/or interact with $PrP^C$.

As used herein, the term "probe that binds to $PrP^C$" includes both direct and indirect binding to $PrP^C$.

As used herein, the term "probe" refers to any agent that binds, directly or indirectly, to a $PrP^C$ protein and is detectable either directly or indirectly.

In one embodiment, the probe is an antibody or antibody fragment that binds to $PrP^C$. Antibodies that bind to $PrP^C$ are well known in the art. Examples of antibodies that bind to $PrP^C$ include antibodies specific for the protein sequence DYEDRYYREN (amino acids 144-153 of the human amino acid sequence, SEQ ID NO:1), optionally monoclonal antibodies specific for the protein sequence DYEDRYYREN. Other examples of antibodies that bind to $PrP^C$ include antibodies that recognize the octo-repeat region located in the N-terminal part of $PrP^C$ (PQGGGGWGQPHGGG-WGQPHGGGWGQPHGGGWGQPHGGGWGQ; residues 51 to 91 of the human amino acid sequence, SEQ ID NO: 2), optionally acetylcholinesterase Fab' conjugates which recognize the octo-repeat region located in the N-terminal part of $PrP^C$. The antibodies may be raised against a preparation of hamster prion protein.

The term "antibody" as used herein is intended to include fragments thereof which also specifically react with $PrP^C$. Antibodies can be fragmented using conventional techniques and the fragments screened for utility in the same manner as described below. For example, $F(ab')_2$ fragments can be generated by treating antibody with pepsin. The resulting F(ab')2 fragment can be treated to reduce disulfide bridges to produce Fab' fragments.

Conventional methods can be used to prepare antibodies. For example, by using a $PrP^C$ or fragment thereof, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (1975) as well as other techniques such as the human B-cell hybridoma technique (Kozbor and Roder, 1983), the EBV-hybridoma technique to produce human monoclonal antibodies (Cole et al., 1985) and screening of combinatorial antibody libraries (Huse et al., 1989). Hybridoma cells can be screened immunochemically for production of antibodies specifically reactive with the peptide and the monoclonal antibodies can be isolated. Therefore, the disclosure also contemplates hybridoma cells secreting monoclonal antibodies with specificity for a $PrP^C$.

Specific antibodies, or antibody fragments, reactive against a $PrP^C$ may also be generated by screening expression libraries encoding immunoglobulin genes, or portions thereof, expressed in bacteria with peptides produced from the nucleic acid molecules encoding $PrP^C$. For example, complete Fab fragments, VH regions and FV regions can be expressed in bacteria using phage expression libraries (See for example Ward et al., 1996, Huse et al., 1989 and McCafferty et al., 1991).

Antibodies may also be prepared using DNA immunization. For example, an expression vector containing a nucleic acid encoding a $PrP^C$ may be injected into a suitable animal such as mouse. The protein will therefore be expressed in vivo and antibodies will be induced. The antibodies can be isolated and prepared as described above for protein immunization.

In one embodiment, the probe comprises a marker or label for detection, such as a radioactive, fluorescent, biological or enzymatic label. In an alternative embodiment, a secondary binding ligand is used, such as a second antibody or biotin/avidin ligand binding agent, as is known in the art for detection of the probe.

The present disclosure provides immunodetection methods in which an antibody contacts a blood sample suspected of having $PrP^C$ under conditions and times that allow immune complexes to form. After this time, the sample-antibody composition is washed to remove any non-specific binding and the formed immune complexes are subsequently detected and/or quantified.

In some embodiments, the amount of $PrP^C$ is quantified, for example, by fluorescence, radioactivity or spectrophotometry depending on the label or marker used. In an embodiment, the amount of $PrP^C$ is quantified by a radioimmunoassay, an enzyme-linked immunoassay, a competitive binding enzyme-linked immunoassay, dot blot, or Western blot, or other assays known in the art.

In one embodiment, the probe is in solution. In another embodiment, the probe is immobilized on a solid support or support pad, such as filter paper, a multiwell plate or a microchip.

Detecting the radioactivity, fluorescence or absorbance of a probe may be accomplished by any method known in the art and may be referred to as "signal detection from the probe". In an embodiment, a FACS analyzer or a microplate reader is used. In another embodiment, a suitable detection technology such as a complementary metal-oxide-semiconductor (CMOS) or charge coupled device (CCD) is used and a unique wavelength of light is applied for illumination of the signal.

In one embodiment, detecting the signal from the probe comprises detecting the intensity or quantity of the signal from the probe and is not attributable to background signal.

In some embodiments, the method further comprises testing a series of known reference standards, such as serially diluted samples containing known amounts of $PrP^C$, optionally, at the same time. The methods optionally further comprise comparing the signal detection of a test subject sample to the signal detection from a reference sample or series of standards of $PrP^C$ of known quantity.

In one embodiment, the reference sample or control is derived from a reference subject who has suffered a brain injury. In another embodiment, reference sample or control is derived from a reference subject who has not suffered a brain injury. The reference sample or standards are optionally tested at the same time as the subject blood sample. In another embodiment, the reference sample or standards are tested at different time from the subject blood sample. As used herein, the term "subject blood sample" refers to a blood sample derived from a test subject.

Correspondence, or similarity, between the signal from a test subject blood sample and the signal from a reference sample from a subject that has suffered a brain injury indicates that the subject has suffered a brain injury. Differences between the signals from the subject sample and the signals from the reference sample from a subject that has suffered a brain injury indicates that the subject has not suffered a brain injury.

Likewise, correspondence, or similarity, between the signal detected from a test subject blood sample and the signal detected from the reference sample from a subject that has not suffered a brain injury indicates that the subject has not suffered a brain injury. Differences between the signal detected from a test subject sample and the signal detected from the reference sample from a subject that has not suffered a brain injury indicates that the subject has suffered a brain injury.

In another embodiment, the identification of an increase in signal detection, optionally a statistically significant increase, of a test subject sample compared to a reference sample from a subject that has not suffered a brain injury indicates that the test subject has suffered a brain injury. In an embodiment, an increase over a cut-off value obtained from historical data from subjects not having suffered a brain injury indicates that the subject has suffered a brain injury.

In another embodiment, the identification of a similar amount of signal detection from a test subject blood sample compared to a reference sample from a subject who has suffered a brain injury or a cut off value obtained from historical data from subjects having suffered a brain injury indicates that the test subject has suffered a brain injury. In one embodiment, a "similar amount" of signal detection refers to no statistically significant difference in signal detection.

In another embodiment, the control is a reference baseline level of $PrP^C$ of the same test subject. In such an embodiment, the reference baseline level is the level of $PrP^C$ in the subject prior to the event that is suspected of causing a brain injury. For example, for an athlete, if the reference baseline level of the athlete is available, the post-concussion value may be compared with the off-season reference baseline level. For a soldier, the reference baseline level may be determined prior to any combat.

In a further embodiment, the control is a reference baseline level of a population of athletes during the off-season. The term "off-season" as used herein refers to the time an athlete refrains from actively competing in a sport, for example, for a hockey player, the off-season is typically during the summer months.

In another embodiment, the control is a reference baseline level of the general population. The term "general population" as used herein refers to healthy same age individuals without any history of TBI. In one embodiment, the subject is a child.

In an embodiment, the reference baseline levels disclosed herein may be obtained from historical data that may be updated as further samples are tested.

A reference value in clinical chemistry refers to an average value of an analyte in at least a sample size of 120 healthy individuals. The International Federation of Clinical Chemistry and Laboratory Medicine (IFCC) recommend a sample size of at least 120 to establish reference values for any analyte (ref: Burtis C A et al. Tietz Textbook of Clinical Chemistry and Molecular Diagnostics, $5^{th}$ Edition 2012, page 106, Elsevier publication).

Increased signal detection can also be quantified. In one embodiment, at least a 5%, 10%, 25%, 50%, 75% or 100% increase in signal detection from subject samples compared to reference samples from a subject who has not suffered a brain injury or such a cut-off value indicates that the test subject has suffered a brain injury. In another embodiment, at least a 5%, 10%, 25%, 50%, 75% or 100% decrease in signal detection from a test subject blood sample compared to reference sample from a subject who has suffered a brain injury or such a cut-off value indicates that the test subject has not suffered a brain injury.

In another embodiment, samples may be obtained at different time points to detect the progression of the brain injury of a subject. Accordingly there is provided a method of monitoring a subject with a brain injury comprising:
(i) (a) contacting a blood sample from the subject obtained at a first time point with a probe that binds to $PrP^C$ and (b) detecting and/or quantifying the amount of $PrP^C$ at the first time point;
(ii) (a) contacting a blood sample from the subject obtained at a second time point with a probe that binds to $PrP^C$ and (b) detecting and/or quantifying the amount of $PrP^C$ at the second time point; and
(iii) comparing the amount of $PrP^C$ from (i) to the amount of $PrP^C$ from (ii), wherein an increase in the amount of $PrP^C$ indicates an increase in the severity of the brain injury and a decrease in the amount of $PrP^C$ indicates an improvement of the brain injury.

In yet another embodiment, there is provided a method of determining whether a subject has suffered a brain injury due to an injury event comprising:
(i) (a) contacting a blood sample from the subject obtained at a first time point prior to the injury event with a probe that binds to $PrP^C$;
(b) detecting and/or quantifying the amount of $PrP^C$ at the first time point;
(ii) (a) contacting a blood sample from the subject obtained at a second time point after the injury event, such as 1-6 days after the injury event, with a probe that binds to $PrP^C$;
(b) detecting and/or quantifying the amount of $PrP^C$ at the second time point; and
(iii) comparing the amount of $PrP^C$ from the first time point with the amount of $PrP^C$ at the second time point; wherein an increase in the amount of $PrP^C$ indicates that the subject has suffered a brain injury due to the injury event.

In one embodiment, the method further comprises obtaining a blood sample from the subject prior to contacting the blood sample with the probe in (i)(a) and/or (ii)(a).

In another embodiment, the first time point provides a baseline level of the subject and the second time point is following the injury event.

In another embodiment, there is provided a method of determining whether a subject has suffered a brain injury due to an injury event comprising:
(i) (a) contacting a blood sample from a subject after the injury event, optionally obtained 1-6 days after, with a probe that binds to $PrP^C$;
(b) detecting and/or quantifying the amount of $PrP^C$ in (a); and
(ii) comparing the amount of $PrP^C$ in (b) with a baseline level of the subject; wherein an increase in the amount of $PrP^C$ from the baseline level indicates that the subject has suffered a brain injury due to the injury event.

In one embodiment, the baseline level of the subject is a pre-combat level of a subject that may be exposed to combat, or an off-season level of a subject that is an athlete that may be prone to a head injury.

The term "injury event" as used herein refers to any incident that causes trauma or force to the head, including without limitation, an explosion, transportation accident or head injury due to a fall or sports-related event.

In one embodiment, the probe is an antibody that specifically binds to $PrP^C$. In one embodiment, the probe comprises a marker or label for detection, such as a radioactive, fluorescent, biological or enzymatic label. In an alternative embodiment, a secondary binding ligand is used, such as a second antibody or biotin/avidin ligand binding agent, as is known in the art for detection of the probe.

In some embodiments, the amount of $PrP^C$ is quantified at each time point, for example, by fluorescence, radioactivity or spectrophotometry depending on the label or marker used. In an embodiment, the amount of $PrP^C$ is quantified at each time point by a radioimmunoassay, an enzyme-linked immunoassay, a competitive binding enzyme-linked immunoassay, dot blot, or Western blot, or other assays known in the art.

In some embodiments, the method further comprises testing a series of known reference standards, such as serially diluted samples containing known amounts of $PrP^C$, optionally, at the same time. The methods optionally further comprise comparing the signal detection of a test subject sample or reference sample to the signal detection from a series of standards of PrP$^C$ of known quantity in order to quantify the amount of PrP$^C$.

In one embodiment, the probe at each time point is in solution. In another embodiment, the probe at each time point is immobilized on a solid support or support pad, such as filter paper, a multiwell plate or a microchip.

In another embodiment, two probes may be used in a sandwich ELISA assay. In such an embodiment, the method comprises:

(a) contacting a blood sample from a test subject with a first probe that binds to PrP$^C$; and (b) contacting the PrP$^C$ bound to the first probe with a second probe that binds to a different part of the PrP$^C$;

wherein the first or second probe is detectable.

In an embodiment, the first probe is an antibody or fragment thereof that specifically binds to PrP$^C$ and is immobilized on a solid support and the second probe is an antibody or fragment thereof that specifically binds to PrP$^C$ at a different epitope than the first probe, is detectable and is in solution. In an alternate embodiment, the first probe is an antibody or fragment thereof that specifically binds to PrP$^C$, is detectable and is in solution and the second probe is an antibody or fragment thereof that specifically binds to PrP$^C$ at a different epitope than the first probe and is immobilized on a solid support. In such embodiments, a double antibody-sandwich technique is applied and (b) the amount of PrP$^C$ in the test subject sample is quantified by comparing to reference standards.

Examples of antibodies that specifically bind to PrP$^C$ and useful as first and second probes are well known in the art. In one embodiment, the first probe is an antibody specific for the encoded protein sequence DYEDRYYREN (SEQ ID NO:1), optionally a monoclonal antibody specific for the protein sequence DYEDRYYREN. In another embodiment, the second probe is an antibody that recognizes the octo-repeat region (PQGGGGWGQPHGGGWGQPHGGG-WGQPHGGGWGQPHGGGWGQ; SEQ ID NO: 2) located in the N-terminal part of PrP$^C$, optionally a acetylcholinesterase Fab' conjugate which recognizes the octo-repeat region located in the N-terminal part of PrP$^C$.

In one embodiment, the detectable probe comprises an enzyme and enzymatic activity can be used to detect and quantify the amount of PrP$^C$. For example, the detectable probe may comprise acetylcholinesterase conjugated to the antibody or antibody fragment and Ellman's reagent can be used to produce a yellow colour which is indicative of the amount of activity of the enzyme, which can be measured by spectrophotometry at an absorbance of 405 nm.

Other examples of detectable probes are well known in the art. For example, in one embodiment, the detectable probe comprises biotin conjugated to the antibody or antibody fragment. Avidin and/or streptavidin, which both bind biotin, can then be used to amplify the detectable signal. Avidin and/or streptavidin can be labelled with reporters including, but not limited to, horse radish peroxidase (HRP) which can hydrolyze 3,3',5,5'-tetramethylbenzidine (TMB), alkaline phosphatase (ALP) which can hydrolyze p-nitrophenyl phosphate (PNPP), beta galactosidase (β-gal) which can hydrolyze 2-nitrophenyl β-D-galactopyranoside (ONPG), and beta lactamase (β-lac) which can hydrolyze ampicillin. The reaction product can be read at specific wavelengths (typically between 400-500 nm). Specific wavelength values are normally provided by the manufacturer or can be determined by a person of skill in the art.

The methods disclosed herein optionally further comprise treating the test subject for the brain injury if the amount of PrP$^C$ is increased compared to a reference sample from a subject not having a brain injury.

For example, patients suffering from brain injury may be treated based on their neurologic status and findings on a CT scan. Large epidural hematomas (>30 ml in volume) and subdural hematomas >10 mm in thickness or associated with more than 5 mm in midline shift may be treated with surgical evacuation. Patients with epidural hematomas and a Glasgow Coma Scale (GCS)≤8 who have pupillary abnormalities and patients with subdural hematomas who have a GCS score 58 or whose GCS score has decreased by ≥2 points from the time of admission may also be treated with surgery. Evacuation of an intracranial hemorrhage may be recommended if it is in the posterior fossa. Open skull fractures and depressed skull fractures, with displacement more than the thickness of the cranium, may also be treated surgically. A course of prophylactic anti-epileptic treatment may be recommended in patients with brain hematomas. The Glasgow Coma Scale measures the level of consciousness in a person following a brain injury.

Accordingly, in another embodiment, the method further comprises treating the subject with surgery, such as surgical evacuation, if a brain injury is detected. In another embodiment, the method further comprises treating the subject with anti-epilepsy drugs if a brain injury is detected.

Having a non-expensive and easy to use diagnostic kit will be a very useful tool to screen victims particularly those with no visible physical signs by the first responders (paramedics, nurses, and doctors) or in clinics and facilities with no CT scan. Considering the fact that in the blast-induced TBI (those who experience the blast force far from epicenter) and sport-related concussions, victims with no apparent physical wound may be ignored or misrepresented, this kit would assist to screen and find invisible victims for further observation/test and treatment. The methods and kits disclosed herein can be used as a supportive tool for more comprehensive CT scan imaging as well.

The present disclosure also provides kits for analyzing blood to detect a brain injury.

In one embodiment, the kit comprises:

(a) a probe that detects the presence or amount of PrP$^C$ in the blood; and (b) instructions for use in detecting brain injury.

In one embodiment, the instructions for use provide instructions on how to perform any of the methods described herein. In another embodiment, the instructions for use provide instruction on further treatment options depending on presence or amount of PrP$^C$.

In one embodiment, the probe is an antibody or antibody fragment that specifically binds to PrP$^C$.

In another embodiment, the kit comprises two probes, an immobilized probe that binds to PrP$^C$ at a first position and a detectable probe that binds to PrP$^C$ at a second position.

In one embodiment, the probe comprises a marker or label for detection, such as a radioactive, fluorescent, biological or enzymatic label. In an alternative embodiment, a secondary binding ligand is used, such as a second antibody or biotin/avidin ligand binding agent, as is known in the art for detection of the probe.

In one embodiment, the kit further comprises serially diluted samples of PrP$^C$ to be used as standards for quantifying the amount of PrP$^C$.

In some embodiments, the amount of PrP$^C$ is quantified, for example, by fluorescence, radioactivity or spectrophotometry depending on the label or marker used and the kit comprises reagents for such detection. In an embodiment, the amount of $PrP^C$ is quantified by a radioimmunoassay, an enzyme-linked immunoassay, a competitive binding enzyme-linked immunoassay, dot blot, or Western blot, or other assays known in the art and the kit comprises reagents for such assays, for example, the kit may comprise Ellman's reagent when the label is the enzyme acetylcholinesterase.

In one embodiment, the probe is in solution. In another embodiment, the probe is immobilized on a solid support or support pad, such as filter paper, a multiwell plate or a microchip.

The methods and kits disclosed herein can be used in conjunction with other tools that diagnose brain injuries, including CT scan imaging and magnetic resonance imaging (MRI).

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

The present inventor hypothesized that blast winds and shock oscillating head acceleration of sufficient intensity can dislodge cellular prion protein $PrP^C$ from neurons into the systemic circulation. $PrP^C$ is an ubiquitously expressed, 208-209 amino acid long, glycophosphatidylinositol (GPI) anchored neuronal lipid raft resident protein, which is highly expressed throughout the central nervous system (Bendheim et al., 1992; Sales et al., 1998; Moser et al., 1995; Aguzzi and Polymenidou 2004). $PrP^C$'s function is not fully understood, but studies have implicated a neuroprotective role (Shmerling et al., 1998; Kuwahara et al., 1999; Mitteregger et al., 2007) in response to hypoxia (McLennan et al., 2004), epilepsy (Walz et al., 1999), neurotoxicity (You et al., 2012) and ischaemic injury (Weise et al., 2004, 2006; Shyu et al., 2005; Spudich et al., 2005). Thus, the loss of $PrP^C$ may be significant as blast-induced ischemia can result from hemorrhaging, air emboli, or even vasovagal innervation.

Male Sprague Dawley (SD) rats (375-400 g) were anesthetized with 3% isoflurane for 3 min in a closed induction chamber. A helium driven shock tube was used at various shock wave pressures (15-30 psi). The exposure system has been developed so that the animals are exposed head only to a "primary blast" that being a single pulse shock wave. The animals were subjected to three varying conditions as follows: control (0 PSI); net, restraint, and whiplash (15-30 PSI) as previously described in Yarnell et al. 2013, incorporated herein by reference (Yarnell et al., 2013). In the "net", "restraint" and "whiplash" conditions, the rats' bodies were secured with tourniquets. To test "whiplash", a pressure blast was used to cause the rat's head and neck to jolt while the rest of the body was restrained. Both head and neck were exposed to the blast. In the "restraint" condition, the neck as well as the body was restrained and only the head was exposed to the blast. In the "net" condition, the rat's body was also fixed in place with a tourniquet and the head was exposed to the blast but a safety net prevented movement of the head and neck. The net absorbed the shock instead of the head and neck. Blood plasma was collected and stored at −80° C.

A qualitative $PrP^C$ enzyme immunometric assay (SPI-BIO, A05201, Paris, FR) was modified for highly sensitive quantification of plasma $PrP^C$ using purified recombinant $PrP^C$ (Prionatis, α-Rec Mouse PrP-RPA0101S, Zurich, CH). The standard provided by SPI-Bio was mixed with milk to-use as a qualitative or semi quantitative tool to screen dairy products which was not suitable for purposes of quantitative analysis of plasma samples. In order to measure absolute $PrP^C$ levels the milk mixed standard (provided by SPI-BIO) was replaced with a pure recombinant prion protein purchased from Prionatis (Prionatis, α-Rec Mouse PrP-RPA0101S, Zurich, CH) and prepared and optimized quantification with serial standard dilutions (0, 0.0625, 0.125, 0.25, and 0.5 ng/ml). The double-antibody sandwich technique was applied, and enzymatic activity of immobilized acetylcholinesterase on Ellman's reagent was measured with spectrophotometry (405 nm). The reaction's color intensity was proportional to plasma $PrP^C$ concentration (ng/ml).

Samples were prepared in a Phosphate Buffered Saline (PBS) Enzymatic Immunometric Assay (EIA) buffer containing 1% BSA (blocking), 10 mM EDTA (metal ion sequestration), 0.1% sodium azide (preservative and antibacterial) and the wash buffer was PBS+Tween-20, pH 7.4.

Results:

All detected plasma $PrP^C$ concentration was measured to ng/mL. All results were statistically analyzed by a statistician using SPSS 19. QQ plot was used to test the normality of the samples. Mann-Whitney U test was used for nonparametric data. Nonparametric data included the whiplash, net, and restraint groups. Two sample independent T test was used for normal data. The normal data was whiplash, net and restraint groups grouped together. When p≤0.05, values were considered statistically different. Pearson's correlation test was used to determine the relationship between the PSI and the prion concentration.

A Q-Q plot graph of net data, restraint data and whiplash is shown in FIG. 1. Most of the data points depart from the normal distribution reference line (y=x) in FIG. 1(a,b,c). Therefore data is not normally distributed and is nonparametric. Therefore, the Mann-Whitney U test is selected to analyse nonparametric data for net, restraint, and whiplash groups (See Table 1, 2, and 3 respectively).

As shown in Table 1, prion concentration between the control and net groups are very similar in mean rank (12.22 vs 12.67). A two tailed test was used to test the null hypothesis that the control group and net group have the same prion concentration levels. There was no statistically significant difference between the control and net groups' prion concentration level (Ucritical=34, Utest=65, P=0.881>0.05).

As shown in Table 2, prion concentration of restraint group is significantly higher than control in mean rank (13.50 vs 7.67). A two tailed test was used to identify if the control and restraint group have different prion concentration levels. There was a statistically significant difference between the control and restraint groups' prion concentration level (Ucritical=26, Utest=24, P=0.033<0.05).

A one tailed test was used to test the hypothesis that restraint groups' prion concentration level was higher than the control group. The restraint group elicited statistically significant higher prion concentrations than the control group (Ucritical=26, Utest=24, p=0.034<0.05). Prion concentration was increased in the restraint group compared to control as a result of the shock delivered by acceleration/deceleration force while restrained.

As shown in Table 3, prion concentration of whiplash group is significantly higher than in control group mean rank (14.09 vs 6.11). A two tailed test was used to identify if the control group and whiplash group has different prion concentration levels. There was a statistically significant difference between the control and whiplash groups' prion concentration level (Ucritical=23, Utest=10, P=0.003<0.05).

A one tailed test was used to test the hypothesis that whiplash groups' prion concentration level was higher than the control group. The whiplash group elicited statistically significant higher prion concentrations than the control group (Ucritical=23, Utest=10, p=0.002<0.05). Since P value is very small (p=0.002), there is very strong evidence to prove that the whiplash group had statistically significant higher prion concentration than control. The present inventor concluded that whiplash group's higher prion concentration is a result of the violent acceleration/deceleration force of being whiplashed, which was strong enough to make a noticeable difference in the prion concentration.

The tri group data points do form a straight line which is the normal reference line (y=x) in FIG. 1(d). This indicates distribution of overall three groups is normal. Therefore, the student T test was selected to analyse parametric data (See Table 4).

As shown in Table 4, the treatment groups elicited a statistically significant higher prion concentration than control (Tcritical=1.679, Ttest=−2.002, p=0.025<0.05). It is suggested to reject the null hypothesis even though it is correct theoretically (p=0.051>0.05). p=0.051 provides weak evidence to support the null hypothesis. One tailed t-test had strong evidence to show that the treatment groups had a statistically higher prion concentration than the control group (p=0.025<0.05). This result also provides a good explanation for the mean prion concentration of the treatment groups being greater than that of control (7.88 ng/mL vs 6.60 ng/mL).

Figure 2:
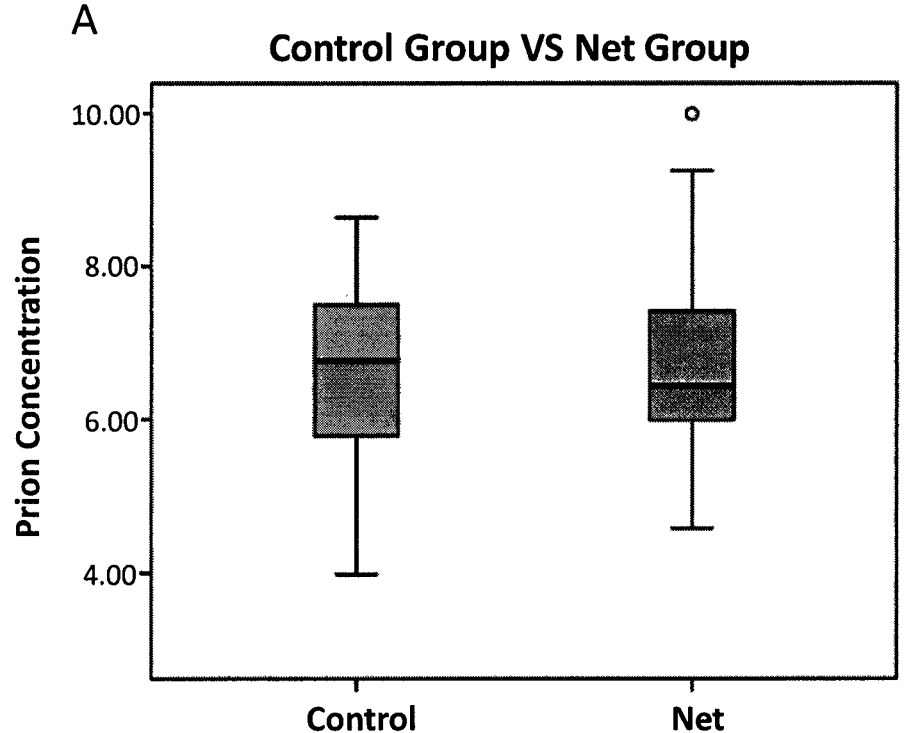
FIG. 2 shows box plots of prion concentration distribution. a) Net data—control (n=9) vs. net (n=15). b) Restraint data—control vs. restraint (n=12). c) Whiplash data—control vs. whiplash (n=11). d) Overall treatment data—control vs. three treatment groups—net, restraint, whiplash (n=38).
Figure 2:
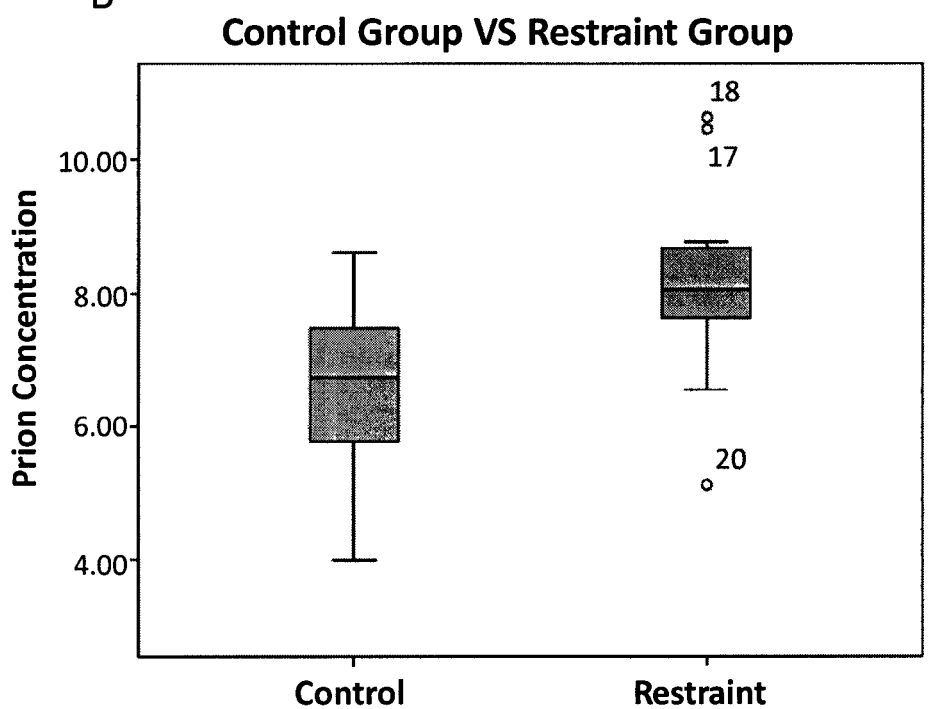
Figure 2:
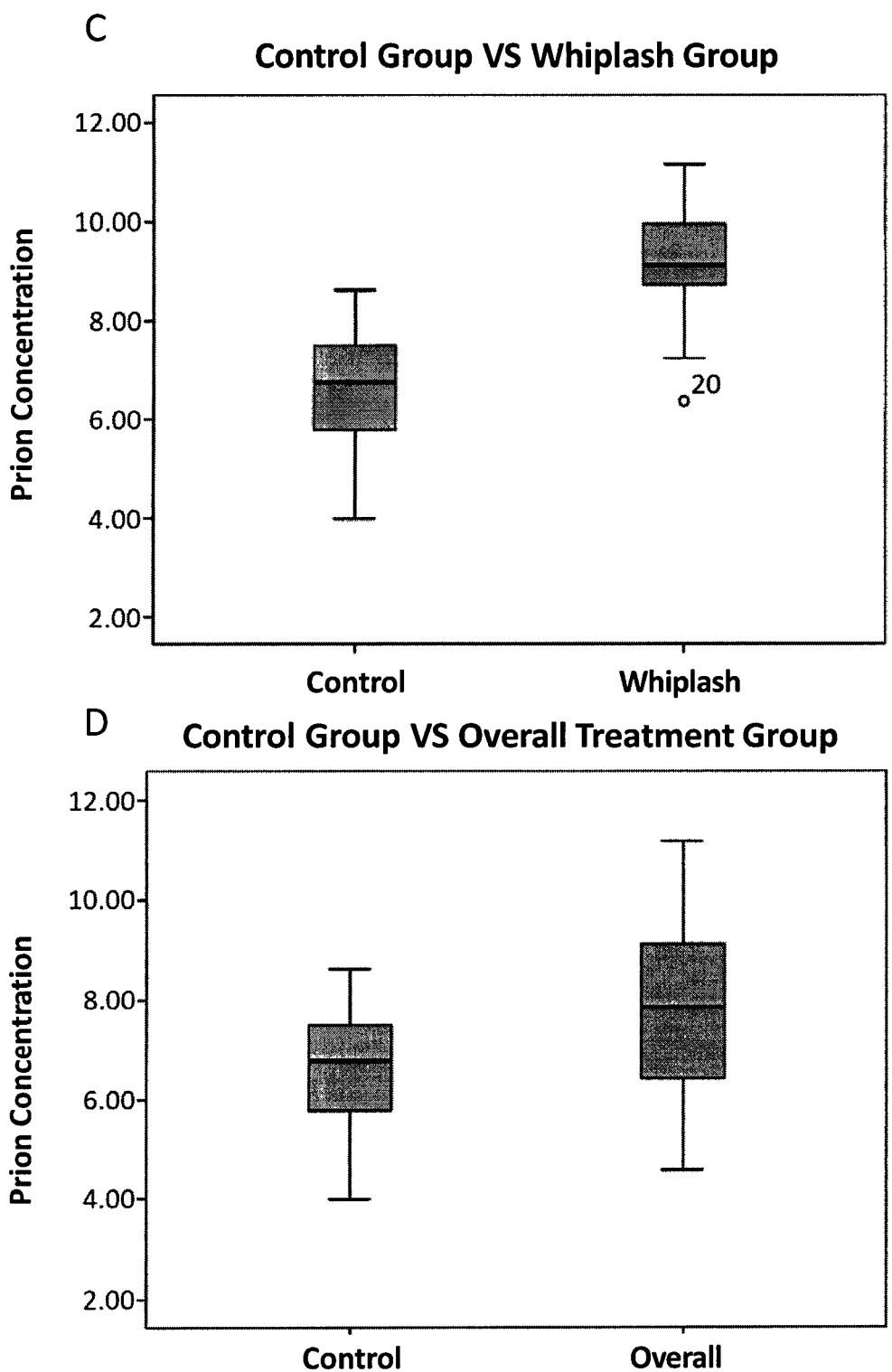
Figure 3:
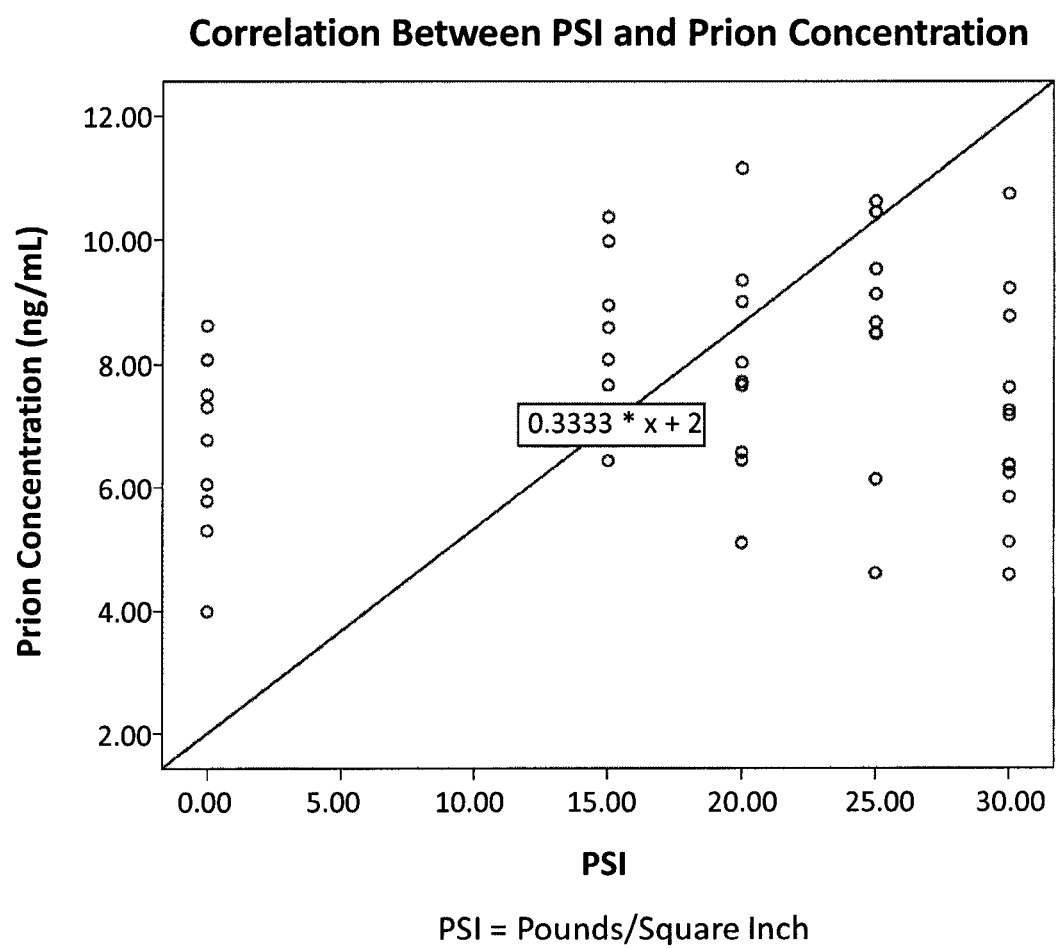
FIG. 3 shows correlation between PSI and prion concentration. Scatterplot analysis was done to determine the correlational relationship between pressure (pounds per square inch-PSI) and prion concentration.

Box plots of prion concentration distribution was analyzed in FIG. 2. Mean and median values of the control group and net group are approximately equal (6.60 ng/mL vs. 6.75 ng/mL) and (6.76 ng/mL vs. 6.43 ng/mL) respectively. This indicates the overall prion concentrations between control and net groups are very similar. This also verifies the null hypothesis, which indicates there was no statistically significant difference between the control and net groups' prion concentration. However, the middle 50% of the net group's distribution of prion concentration is shifted above that of the control group. It is possible that the net group has slightly higher prion concentration than control as a result of weak shock strength, but not enough to elicit significant differences (p=0.881>0.05).

Mean and median values of the restraint group were significantly higher than of control (8.15 ng/mL vs. 6.60 ng/mL) and (8.05 ng/mL vs. 6.76 ng/mL) respectively. Roughly 99% of the restraint group's distribution of prion concentration is shifted above the median of the control group. This is a good indication that prion concentration in the restraint group is significantly higher than in control group. This also verifies the test result of the alternative hypothesis, which indicates that the restraint group has statistically significant higher prion concentrations than the control group ($p=0.034<0.05$). Data points 17, 18, and 20 are outliers.

Mean and median values of the whiplash group were significantly higher than of control (9.13 ng/mL vs. 6.60 ng/mL) and (9.14 ng/mL vs. 6.76 ng/mL) respectively. All concentration points are above control. This is good indication that prion concentration in the whiplash group is significantly higher than in control group. This also verifies the test result of the alternative hypothesis, which indicates that the whiplash group elicited statistically significant higher prion concentrations than control ($p=0.002<0.05$). Data point 20 is an outlier.

Three quarter of tri group data are shifted above the median of control group. The above facts show that accepting the null hypothesis does not provide a good explanation. Though theoretically, it is correct to not reject the null hypothesis when $p>0.05$. In order to find reasonable explanation, a one tailed t test was conducted (See Table 4). The test result was the three treatment groups had statistically higher mean and median prion concentration than the control group (7.88 ng/mL vs. 6.60 ng/mL) and (7.87 ng/mL vs. 6.76 ng/mL).

Scatterplot analysis was done to determine the correlational relationship between pressure (pounds per square inch-PSI) and prion concentration (FIG. 3). There is a positive correlation (prion Concentration=0.3333*PSI+2), showing that when PSI increases in value, prion concentration increases in value as well (See Table 5).

Discussion

The present inventor for the first time has established a statistically significant general link between the blast-induced TBI and plasma level of $PrP^C$. This connection is particularly strong and evident among the experimental animals (whiplash and restraint group) subjected to blast-induced TBI. These findings make it possible to use a small sample of plasma from people, soldiers and civilians, exposed to any type of blast to assess conditions of the victims in terms of the possibility of developing TBI, particularly in victims with none or few visible physical signs and symptoms, based on $PrP^C$ levels. This new marker will also assist medical personnel to make decision on the immediate and long-term treatment and follow-up of the blast-TBI victims. It can also be used as a complementary test along with more sophisticated medical tests such as MRI.

Having a non-expensive, and easy to use diagnostic kit such as $PrP^C$ based quantitative ELISA kit, will be a very useful tool to screen victims particularly those with no visible physical signs by the first responders (paramedics, nurses, and doctors) or in clinics and facilities with no CT scan. Considering the fact that in the blast-induced TBI (those who experience the blast force far from epicenter) and sport-related concussions, victims with no apparent physical wound may be ignored or mis-represented, this kit would assist to screen and find invisible victims for further observation/test and treatment. Finally this kit can be used as a supportive tool for more comprehensive CT scan imaging as well.

For example, two different measuring devices are envisioned:

The first would be a simple and easy to use diagnostic kit with a sandwich ELISA lateral flow format for the first responders such as medics, coaches, and emergency personnel. In brief, the plasma samples first come in touch with colored particles labeled with antibody raised against $PrP^C$ (target analyte). An antibody raised against different epitope of $PrP^C$ will be used in the test line. The test line will also show a colorful band. The intensity of this band correlates with $PrP^C$ levels. This simple kit will come with a band color intensity meter to assist the judgment on $PrP^C$ level.

The second would be a quantitative device: In this device the intensity of the test line will be measured to determine the quantity of PrP$^C$ in the sample. A lateral flow reader (a handheld diagnostic device) will be used to provide a fully quantitative assay result. Using a suitable detection technology (CMOS or CCD) and unique wavelength of light for illumination, one can obtain a signal rich image from the actual test lines. With an image processing algorithm specifically designed for a PrP$^C$ Elisa measurement, line intensities can then be converted to PrP$^C$ concentrations. This quantitative lateral flow device can be used in the field hospitals and clinics, as well as diagnostic medical laboratories.

Example 2

Adult male Sprague-Dawley (SD) rats were exposed to controlled single pulse shock waves closely simulating free field blast (restraint) (see Ritzel et al., 2011) and blood plasma was collected afterwards for quantification of PrP$^C$. (Ritzel et al., 2011) to establish plasma PrP$^C$ as a potential biomarker for primary bTBI and to establish a positive correlation between plasma PrP$^C$ and blast wave intensity exposure.
Methods
Advanced Blast Simulator (ABS)

A custom-built ABS (approx. 30.5 cm in diameter and 5.79 m in length) located at DRDC Suffield was used for producing simulated blast waves (Ritzel et al., 2011). The ABS consisted of a "driver" section filled with high-pressure gas, and a low-pressure test section, separated by a frangible cellulose acetate diaphragm. Closely controlled pressurization of the driver causes rupture of the diaphragm, releasing high-pressure gas into the test section, and generating a shock wave down the length of the test section. The inclusion of a custom designed divergent driver and an End Wave Eliminator in this ABS system, enables the highly reproducible generation of single pulse shock waves (Ritzel et al., 2011). Compressed helium and varying thickness of cellulose acetate sheets were employed to obtain the desired target pressure.
Animal Exposure to Simulated Blast (Restraint)

Adult male Sprague-Dawley rats were acquired from Charles River Laboratories (St. Constant, Que, Canada) and acclimated for at least one week prior to exposure. The animals were kept on a 12 hour light/dark cycle and fed ad libitum. On the day of use, the animals (~350-400 g) were anaesthetized with 3% isoflurane in oxygen for 3 min in a closed induction chamber. Anesthesia was maintained using a face mask and the animal was placed into a restraint consisting of a clear plastic cylindrical sleeve, with the neck encircled in a closely fitting plastic collar with the head protruding from the end (i.e. the restraint position described above). The hind quarters were supported using an end cap fitted with a piston. To the left of the head, a mesh netting was secured between two pins placed vertically in line with the side of, and above and below the head. The head was placed against this vertical netting, and then held in place using additional netting around the head. This was locked into place using Velcro on the side of the head opposite the direction of shock wave propagation. After a minimum of 8 min of anesthetic exposure, the cylindrical restraint containing the animal was set into the wall of the ABS, such that only the head protruded into the test section. Test groups consisted of sham control, and head-only, side-on exposures of single pulse shock wave overpressures of 15, 20, 25 and 30 pounds per square inch (PSI) or 103.4, 137.9, 172.4, 206.8 kilopascal (kPa). After exposure, the animal was immediately removed from the shock tube and animal restraint, and closely observed for at least 30 min post-exposure, or until no signs of stress were evident. The animals were returned to the dedicated animal holding facility where they had been observed on a daily basis prior to testing. At 24 hours the animals were anaesthetized and euthanized by decapitation prior to blood sample collection.
Sample Collection Following anesthesia, whole trunk blood samples were collected from both control (n=19) and blast (n=33) group rats following decapitation into K2EDTA coated blood collection tubes. Samples were centrifuged for 10 minutes at 2,000×g and the separated plasma supernatant was collected. To avoid excessive freeze-thaw cycles, blood plasma aliquots were made and stored at −20° C. for short-term use and the rest stored at −80° C.
Plasma PrP$^C$ ELISA For sensitive quantification of full-length soluble PrP$^C$, an ELISA technique was employed using a commercially available assay kit (Spi Bio A05201, Paris, FR). The kit is typically used for qualitative screening in animal products; therefore the manufacturer's protocol was modified to allow sensitive and accurate quantification. Pure full-length recombinant PrP$^C$ (Prionatis, α-Rec Mouse PrP-RPA0101S, Zurich, CH) was used for producing serial dilutions (0.625-20 ng/mL) in order to establish the calibration curve for quantifying samples. All samples and PrP$^C$ protein standards were diluted in the manufacturer's provided dilution buffer solution (1 M phosphate, 1% BSA, 4 M NaCl, 10 mM EDTA, and 0.1% sodium azide). Remaining solutions and reagents provided by the manufacturer were reconstituted and prepared according to the suggested protocol. Briefly, overall protein concentration of individual samples was first determined in triplicate using the Bio-Rad DC protein assay (Sigma-Aldrich, bovine albumin, A-9647, Oakville ON). Samples and standards were loaded in equal volume in triplicate in the kit's 96 microwell plate strips. Diluted samples were loaded as such that each well contained approximately overall protein amounts of approximately 75-100 µg. The plate was then incubated overnight at 4° C. with shaking to allow adequate antigen binding to well-embedded monoclonal antibodies, specific to the 144-153 amino acid sequence. After rigorous washing (4M phosphate, pH 7.4), the wells were incubated with an acetylcholinesterase-(AChE) Fab' conjugated antibody solution for two hours at RT with shaking, thus completing a double-antibody sandwich. After another cycle of rigorous washing, Eliman's reagent was added in equal volume to each well, and incubated in the dark for 30 minutes at RT with shaking. Any immobilized AChE-conjugated antibody bound to PrP$^C$ therefore reacted with Ellman's reagent to produce a colorimetric reaction in solution proportional to the concentration of PrP$^C$, which was read using a microplate reader at 405 nm (Molecular Devices, LLC., SpectraMax M5, Sunnyvale Calif., USA). Raw absorbance values were interpolated along the standard calibration curve and converted into PrP$^C$ concentration values.
PrP$^C$ Western Blotting Western blotting was conducted as previously described (Taghibiglou et al., 2011). Briefly, diluted plasma samples were separated with SDS-PAGE, transferred onto a PVDF membrane, and probed with an anti-PrP$^C$ primary antibody (Santa Cruz, goat IgG anti-PrP C-20 pAb, 1:500, sc-7693). For sequential reprobing of the same blots, the membranes were stripped and subjected to immunoblotting with glyceraldehyde-3-phosphate dehydrogenase (GAPDH) primary antibody (AbCam, mouse IgG2b mAb, 1:2000, ab9484). Blots were developed using enhanced chemiluminescence detection (Amersham) and exposed to x-ray film. Band intensities were quantified using NIH ImageJ software and normalized to the quantity of GAPDH in each sample lane.

Statistical Analysis

Statistical analysis for all data was performed using the IBM SPSS 21 Statistical package. Non-parametric data was appropriately analyzed using the Kruskall-Wallis test for comparison of mean rank values of control and the different blast intensity groups. Post-hoc Mann-Whitney U-test with a Bonferroni correction for 95% level of confidence was used for determining statistical significance between mean rank values of control and individual blast group $PrP^C$ concentration. The Jonckheere trend test was used to determine a significant relationship between blast intensity and $PrP^C$ concentration. Kendall's tau b test determined the nature and degree of association for said relationship. Receiver operating characteristics (ROC) analysis was performed for determining accuracy of classifier performance. The measure of general predictiveness of classifiers was determined by area under the ROC curve (AUC). Two-graph ROC (TG-ROC) analysis was used for determining the cut-off value, as described by Greiner et al., between control and blast exposure groups, and positive and negative predictive values (PPV and NPV) were subsequently calculated. (Greiner et al., 1995) For all tests, statistical significance was determined when $p \leq 0.05$.

Results

The use of the ABS system, in concert with the head restraint configuration employed in this Example has been shown to minimize concussive and whiplash forces and produce a "clean" primary single pulse shockwave insult. The overpressures obtained for the four test groups were: 15±0.2, 20±0.8, 25±0.3 and 30±0.9 psi (mean±SD). Immediately after exposure, the animals showed no obvious signs of injury and revived from the anesthetic with no visible differences compared to sham controls with respect to time to revival and time to mobility. No signs of distress or injury were noted either immediately after regaining consciousness after exposure, or the following day.

Figure 7:
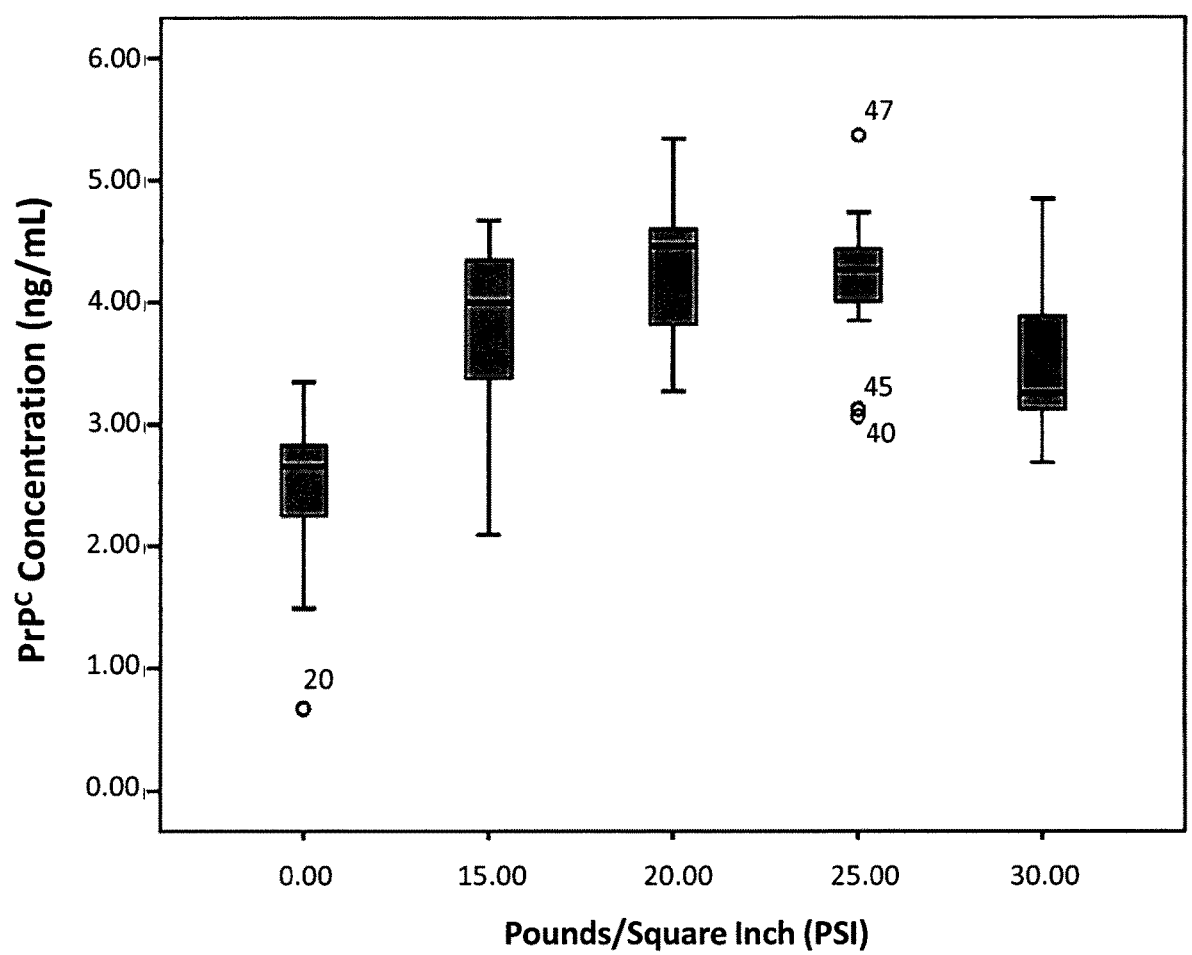
FIG. 7 shows a box plot comparison of control (0 PSI n=19) and blast (15 PSI n=7; 20 PSI n=7; 25 PSI n=12; 30 PSI n=7) groups illustrating that the majority of blast group $PrP^C$ concentrations (interquartile range Q1-Q3) lie above the median (Q2) of the control group. Data points 20, 40, 45, and 47 are considered outliers from group distribution.

Quantitative analysis of blood plasma $PrP^C$ from both control (n=19, 0 PSI) and blast (n=33, 15-30 PSI) groups was performed using a modified commercial ELISA kit specific for $PrP^C$; for results summary (see Table 7). Graphical representation of $PrP^C$ concentration results is provided in box-and-whisker plot (see FIG. 7) showing the majority of blast group values lie above the control group median value (2.66 ng/mL), indicating that blast group concentrations are distinct from control results. Quantile-quantile (Q-Q) plot of blast group results distribution reveals that most data points deviate from the normal distribution line (y=x) and therefore this data is considered non-parametric. As such, the Kruskall-Wallis test for non-parametric was appropriately used for determining differences in $PrP^C$ concentration mean rank values of sham controls and individual blast intensity groups. There was a statistically significant difference ($\chi2=31.62$, $p<0.0001$) between sham control (mean rank=11.84, n=19), 15 PSI (mean rank=31.14, n=7), 20 PSI (mean rank=40.00, n=7), 25 PSI (mean rank=37.58, n=12), and 30 PSI (mean rank=29.14, n=7) blast exposure groups. Post-hoc Mann-Whitney U-test with a Bonferroni correction for multiple comparisons with an adjusted level of significance ($\alpha=0.0125$) determined statistical difference of $PrP^C$ concentration mean rank between sham controls and 15 PSI (10.89 vs. 20.57, U=17, p=0.004), 20 PSI (10.05 vs. 22.86, U=1, p=0.0001), 25 PSI (10.16 vs. 25.25, U=3, p<0.0001), and 30 PSI (10.74 vs. 21.00, U=14, p=0.002) blast exposure groups.

Figure 8:
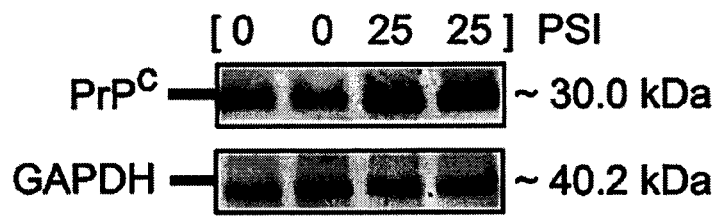
FIG. 8 shows A) a Western blot of $PrP^C$. Results are semi-quantitative and are for the purpose of simple visualization of increased $PrP^C$ in blast group plasma compared with control. B) The numerical (fold) change bar graph represents a mean fold increase of 1.60±0.41 compared with control values, given an arbitrary value of 1.0 (n=4, 2-tailed test p<0.05).
Figure 8:
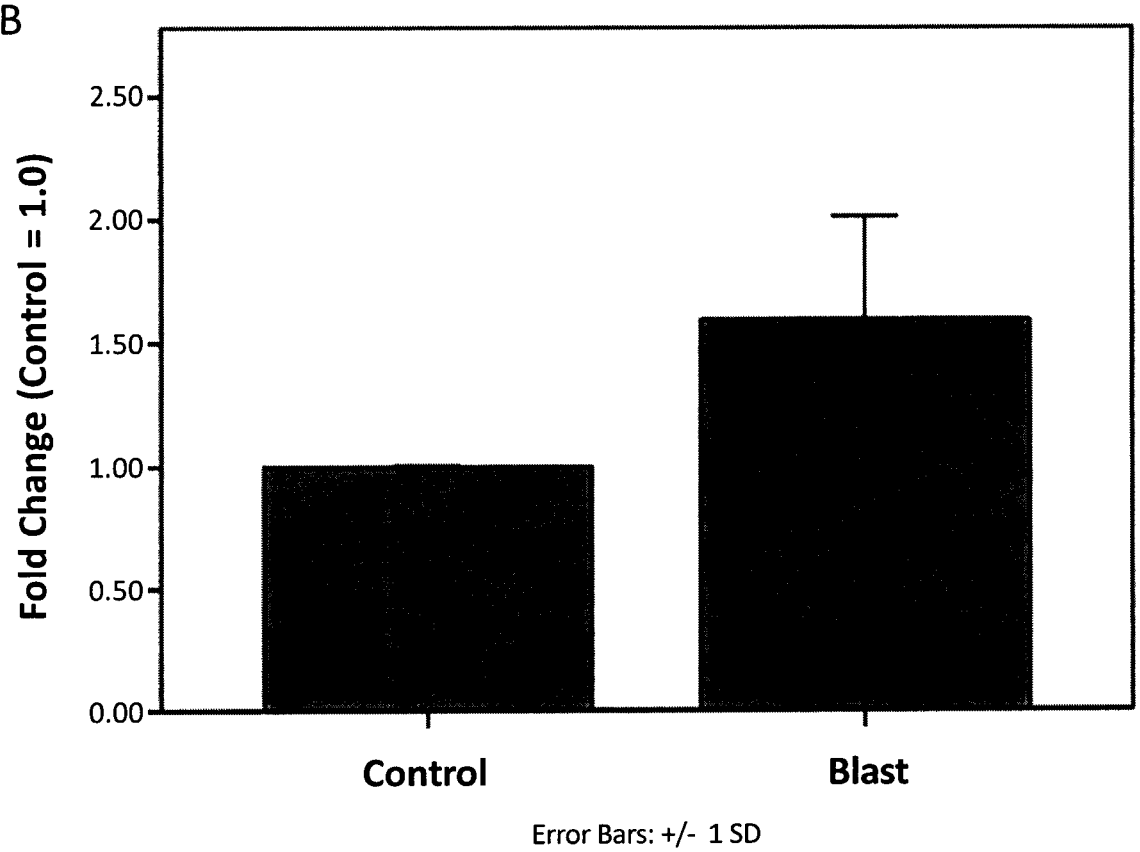

Quantified differences between blast and control group $PrP^C$ concentration was demonstrated with Western blotting (see FIG. 8). Densitometric analysis using NIH Image J software calculated $PrP^C$ band intensity in relation to GAPDH loading control in blast group plasma determined a 1.60±0.41 fold increase (n=4, 2-tailed test p<0.001) when compared with controls. To determine a significant relationship between increasing blast pressure intensity (PSI) and plasma $PrP^C$ content, Jonckheere's trend test was used that showed an ordered relationship between blast intensity and $PrP^C$ concentration (J-T=773.00, p<0.0001).

Additionally, Kendall's tau b test determined the correlation coefficient at 0.446 (p<0.0001) reflecting a positive trend association between increasing blast intensity groups and their respective median $PrP^C$ concentrations.

ROC analysis was performed for determining accuracy of the ELISA test based on the predictiveness of control and blast group classifiers. ROC analysis allowed comparison of $PrP^C$ sensitivity against the inverse specificity over a range of thresholds for evaluating overall test accuracy. The AUC was determined at 0.944±0.032 S.E. (95% CI, 0.881-1.000, p<0.0001) indicating ELISA test results as highly accurate for distinguishing between control and blast groups. As there is presently no standard reference database available for rat plasma $PrP^C$, TG-ROC analysis was performed using values obtained to determine the minimum cutoff value defining blast exposure. A conservative cutoff of 2.78 ng/mL was chosen which yielded 79.1% sensitivity and specificity, 81.6% PPV, and 85.7% NPV.

Discussion

Increased blast exposure during the recent military conflicts in Afghanistan and Iraq has not surprisingly been concomitant with increased reports of TBI among service members (Hoge et al., 2008; Warden 2006; Okie 2005). TBI is typically brought upon by direct impact or acceleration forces to the head leading to collision between the brain and skull as well as shearing strain on brain tissue and vasculature (Rosenfeld et al., 2013; Barkhoudarian et al., 2011). Proper diagnosis of TBI due to blast is especially difficult given the potential absence of physical symptoms or presence of nonspecific ones, thus confounding the recognition of mild indications such as sleep disturbance, fatigue, headaches, and loss of concentration that are often overlooked and underreported by service members (Tanielian and Jaycox 2008; DeKosky et al., 2010). A possible approach towards addressing this issue is in screening individuals for protein biomarkers specific for bTBI. Various proteins have been investigated, but none has been conclusively established as having clinically practical screening qualities (Agoston et al., 2009; Agoston et al., 2012). For instance the S100B protein is frequently used as a biomarker for TBI and has been thoroughly investigated because of its strong NPV; however its value for predicting TBI outcome is questionable because of its high correlation with bone fractures without TBI, extracranial injury, and even melanoma (Unden et al., 2005; Savola et al., 2004; Anderson et al., 2001; Harpio, and Einarsson 2004). Another protein, GFAP, has shown correlation with TBI outcome, but has been inconsistent in discerning between TBI and non-injured victims (Metting et al., 2012).

As such, investigation towards establishing both a highly predictive and reliable protein biomarker has continued. Thus, in collaboration with the DRDC, Suffield Research Center, the present inventor sought to establish the use of a novel protein biomarker, the PrP$^C$, within the blood plasma of rats exposed to simulated primary blast. This is the shock wave component of a blast, and is distinct from the other blast components that may cause injury such as penetrating fragments (secondary), blast wind effects (tertiary) and noxious gases, heat, dust, etc. (quaternary). Due to technical difficulties the experimental replication of clean primary blast conditions has traditionally been problematic. However, recent developments in these laboratories (see Ritzel et al., 2011) have enabled the consistent replication of single pulse shock waves with minimal concussive and whiplash forces, that is highly reminiscent of a free field blast (Ritzel et al., 2011). Adult male SD rats were subjected to single pulse shock waves of varying intensities localized only to the head in order to determine whether there was an appreciable rise in plasma PrP$^C$ concentration, which was quantified using a modified commercial ELISA kit. Without wishing to be bound by theory, the present inventor hypothesized that the blast-induced shearing forces as described by Schardin (Schardin, 1955) could cause the predominantly extracellular, GPI anchored PrP$^C$ to be dislodged from its neuronal lipid rafts location. Previous reports have shown increased plasma PrP$^C$ concentration following stroke and in patients with various neurodegenerative diseases (Mitsios, et al., 2007; Volkel et al., 2001). Additionally, there is a growing body of evidence reporting neurodegenerative changes post-TBI, which may possibly allude to an association with elevated plasma PrP$^C$ levels (Smith et al., 2003; Uryu et al., 2003; Sidaros et al., 2009; Stern et al., 2011; Small et al., 2013; Johnson et al., 2013). In the present Example, the present inventor identified the rise in plasma levels of PrP$^C$ as a novel biomarker for detection of primary bTBI; and based on current literature search, this is the first report of such an association. Statistical analysis determined that mean PrP$^C$ concentration in simulated primary blast exposed rats was significantly greater than control. Moreover, a mild positive correlation between plasma PrP$^C$ levels and increasing blast intensity (PSI) was also determined. Results showed dramatic increase of plasma PrP$^C$ in the 15 and 20 PSI blast group, with levels plateauing at higher intensities. In this regard, this initial finding suggests that subjects exposed to lower blast intensity elicit a similar plasma PrP$^C$ profile to those at higher magnitudes. These findings are in agreement with immunohistochemical staining for neurofilament phosphorylation. The translation of this finding to humans may mean that military service members exposed to primary blast waves only, including those at lower intensities, experience a similar effect to those at higher intensity, but may not receive medical attention due to lack of apparent injuries. Immunoblotting additionally confirmed, albeit semi-quantitatively, that there is an apparent increase in plasma PrP$^C$ content after blast exposure compared with control, which is consistent with quantitative ELISA results obtained. The PrP$^C$ concentration cutoff value for blast exposure was determined conservatively at 2.78 ng/mL (79.1% sensitivity and specificity; 81.6% PPV; and 85.7% NPV). It is noteworthy that there is currently no known standard reference database for normal rat plasma PrP$^C$ concentrations, therefore the cutoff value determined is based from the normal concentration values that were established. In summary, without wishing to be bound by theory, the present findings support the working hypothesis that a primary blast force of sufficient intensity passing through brain tissue may dislodge the loosely attached PrP$^C$ from its extracellular domain, which subsequently accumulates within the systemic circulation.

The neuropathology of bTBI is not entirely clear, but reports have noted among other symptoms, brain edema, cerebral pseudoaneurysms, intracerebral hemorrhaging, microlesions, cell death, and axonal injury as a result of blast exposure (Ling et al., 2009; Krupinski et al., 2008; Starke et al., 2002; Simak et al., 2002). Such evidence establishes the basis that blast exposure can cause damage to brain tissue and vasculature. Furthermore, recent studies have shown that patients with cerebrovascular disease or vascular endothelial damage had higher levels of plasma PrP$^C$ than control values (Krupinski et al., 2008; Starke et al., 2002; Simak et al., 2002). At this time, it is not possible to discern whether the observation of increased plasma PrP$^C$ following primary blast exposure is exclusively of neural origin or if it also arises from the surrounding cerebrovasculature, which may also be subjected to primary blast-induced damage. Furthermore, the PrP$^C$ has been reported to be upregulated following focal cerebral ischemia, therefore it is possible that the rise in plasma PrP$^C$ content may be partially attributed to damaged ischemic regions in the brain as a result of blast exposure (Weise et al., 2004).

The rise in PrP$^C$ concentration is yet another part of the unique pathology complex associated with primary bTBI. In relation to primary bTBI, the neuroprotective function of PrP$^C$ may be of interest as studies have noted its involvement in the context of hypoxia, epilepsy, oxidative stress, neurotoxicity, ischemic injury, and even in limiting brain damage in an animal model of TBI (Weise et al., 2004; McLennan et al., 2004; Walz et al., 1999; Milhavet et al., 2000; Rangel et al., 2007; You et al., 2012, Weise et al., 2006; Shyu et al. 2005; Spudich et al. 2005; Hoshino et al., 2003).

Example 3

Because of the PrP$^C$'s extracellular orientation, it is possible that during a concussive event, linear and/or rotational forces transmitted to the brain may cause the tenuously bound PrP$^C$ to dislodge and collect within the systemic circulation. In this Example, this hypothesis was addressed by collecting blood plasma from the normal healthy university student population (age 18-30 years old) as well as concussive student athletes for quantification of PrP$^C$. Plasma PrP$^C$ was identified as a potential biomarker for sport-related concussions.
Material and Methods
Athletes and Non-Athletes Recruitment Participants of high-contact sports were recruited as follows: 17 ice hockey, 20 football, 4 soccer, 18 basketball players, and 6 wrestlers. Samples were also collected from athletes in typically low contact sports such as volleyball and cross country. For normal values, 27 samples were collected from the non-athlete university student population. In total six concussive athletes were identified using the sports concussion assessment tool (SCAT3) concussion assessment criteria (Guskiewicz et al., 2013) and their post-concussion blood samples collected 1-6 days post-incidence depending on the subject's availability. For the summary characteristics of participants involved in this study see Table 6.
Plasma Separation Samples were alphanumerically coded and sample testing was performed single blinded. A small sample of venous blood (2 mL) was collected from both athletes and non-athletes into lithium heparin coated vacutainer tubes (BD vacutainer PST, #367962). Samples were centrifuged at 10,000 G for 10 minutes for plasma isolation. Plasma was aliquoted and stored at −80° C. for future analysis.

Plasma PrP$^C$ ELISA

For sensitive quantification of full-length soluble PrP$^C$, an ELISA technique was employed using a commercially available qualitative assay kit (Spi Bio A05201, Paris, FR) and the manufacturer's protocol was modified to allow sensitive and accurate quantification. Pure full-length recombinant PrP$^C$ (Prionatis, α-Rec Mouse PrP-RPA0101S, Zurich, CH) was used for producing serial dilutions (0.625-20 ng/mL) in order to establish the calibration curve for quantifying samples. All samples and PrP$^C$ protein standards were diluted in the manufacturer's provided dilution buffer solution (1 M phosphate, 1% BSA, 4 M NaCl, 10 mM EDTA, and 0.1% sodium azide). Remaining solutions and reagents provided by the manufacturer were reconstituted and prepared according to the suggested protocol. Briefly, overall protein concentration of individual samples was first determined in triplicate using the Bio-Rad DC protein assay (Sigma-Aldrich, bovine albumin, A-9647, Oakville ON). Samples and standards were loaded in equal volume in triplicate in the kit's 96 microwell plate strips. Diluted samples were loaded as such that each well contained approximately overall protein amounts of 75-100 μg. The plate was then incubated overnight at 4° C. with shaking to allow adequate antigen binding to well-embedded monoclonal antibodies (specific to the 144-153 amino acid sequence (SPI Biotech, Paris France)). After rigorous washing (4M phosphate, pH 7.4), the wells were incubated with an acetylcholinesterase-(AChE) Fab' conjugated antibody solution for two hours at RT with shaking, thus completing a double-antibody sandwich. After another cycle of rigorous washing, Ellman's reagent was added in equal volume to each well, and incubated in the dark for 30 minutes at RT with shaking. Any immobilized AChE-conjugated antibody bound to PrP$^C$ therefore reacted with Ellman's reagent to produce a colorimetric reaction in solution proportional to the concentration of PrP$^C$, which was read using a microplate reader at 405 nm (Molecular Devices, LLC., SpectraMax M5, Sunnyvale Calif., USA). Raw absorbance values were interpolated along the standard calibration curve and converted into PrP$^C$ concentration values.

Statistical Analysis

Statistical analysis for all data was performed using Graphpad Prism 5 statistical package. Student's T-test for statistical significance was performed for plasma PrP$^C$ mean value comparison of the following groupings: male vs. female, athletes vs. non-athletes, and post-TBI vs. baseline or combined athletes and non-athletes (representative of the general population). One-way analysis of variance (one-way ANOVA) was used to determine whether there is significant variation of mean PrP$^C$ concentration among different age groups. Results were considered statistically significant when p 5.0.05.

Results

Figure 4:
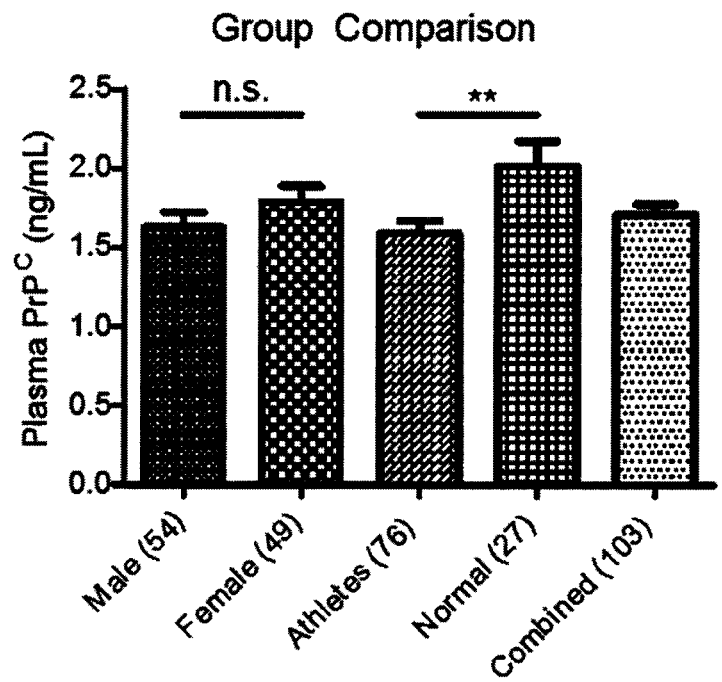
FIG. 4 shows a two-tailed unpaired student's t-test showing no significant difference between male (n=54, 1.63 ng/mL±0.10 SEM) and female (n=49, 1.79 ng/mL±0.10 SEM) (p=0.2578). T test of athletes (n=76, 1.59 ng/mL±0.07 SEM) vs. the normal non-athlete population (n=27, 2.02 ng/mL±0.15 SEM) shows significant difference between mean $PrP^C$ concentrations (p<0.01).

Plasma Levels of Soluble Cellular Prion Protein Levels in Healthy Young Male and Female Adults In order to investigate the possibility that the plasma level of PrP$^C$ rises following mTBI, normal soluble PrP$^C$ levels were first measured in the general population aged 18 years and above without significant confounds due to illness, health condition, or concussion within the past six months. T-test comparison between male (mean±SEM=1.63 ng/mL±0.10, n=54) vs. female (1.79 ng/mL±0.10, n=49) showed no significant difference in mean concentration of plasma PrP$^C$ (p>0.05) (see FIG. 4). Additionally, a slight significant difference was found in mean plasma PrP$^C$ between off season athletes' baselines (1.59±0.073, n=76) vs. normal non-athlete students (2.012±0.15, n=27) (p<0.01) (see FIG. 4).

Figure 5:
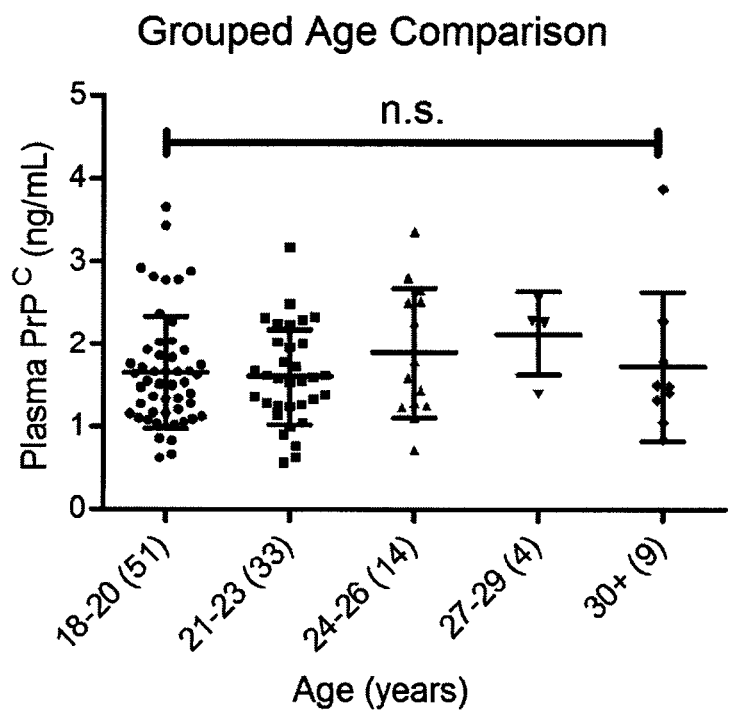
FIG. 5 shows a one-way ANOVA of $PrP^C$ concentrations for different age groups showing there is no significant difference between mean concentrations for subjects between the ages of 18-20 (n=51, 1.66 ng/mL±0.68 SD), 21-33 (n=33, 1.61 ng/L±0.58 SD), 24-26 (n=14, 1.89 ng/mL±0.78 SD), 27-29 (n=4, 2.13 ng/mL±0.51 SD), and those 30 and over (n=9, 1.73 ng/mL±0.90 SD) (p=0.4702).

Furthermore, aggregate results were grouped within five age groups to determine any significant difference in plasma PrP$^C$ across different age brackets (see FIG. 5). One-way ANOVA for determining variation between mean plasma PrP$^C$ concentration across age groups showed no significant difference across the different age groups (p>0.05).

Plasma Soluble PrP$^C$ Level Increases in Concussive Athletes

Figure 6:
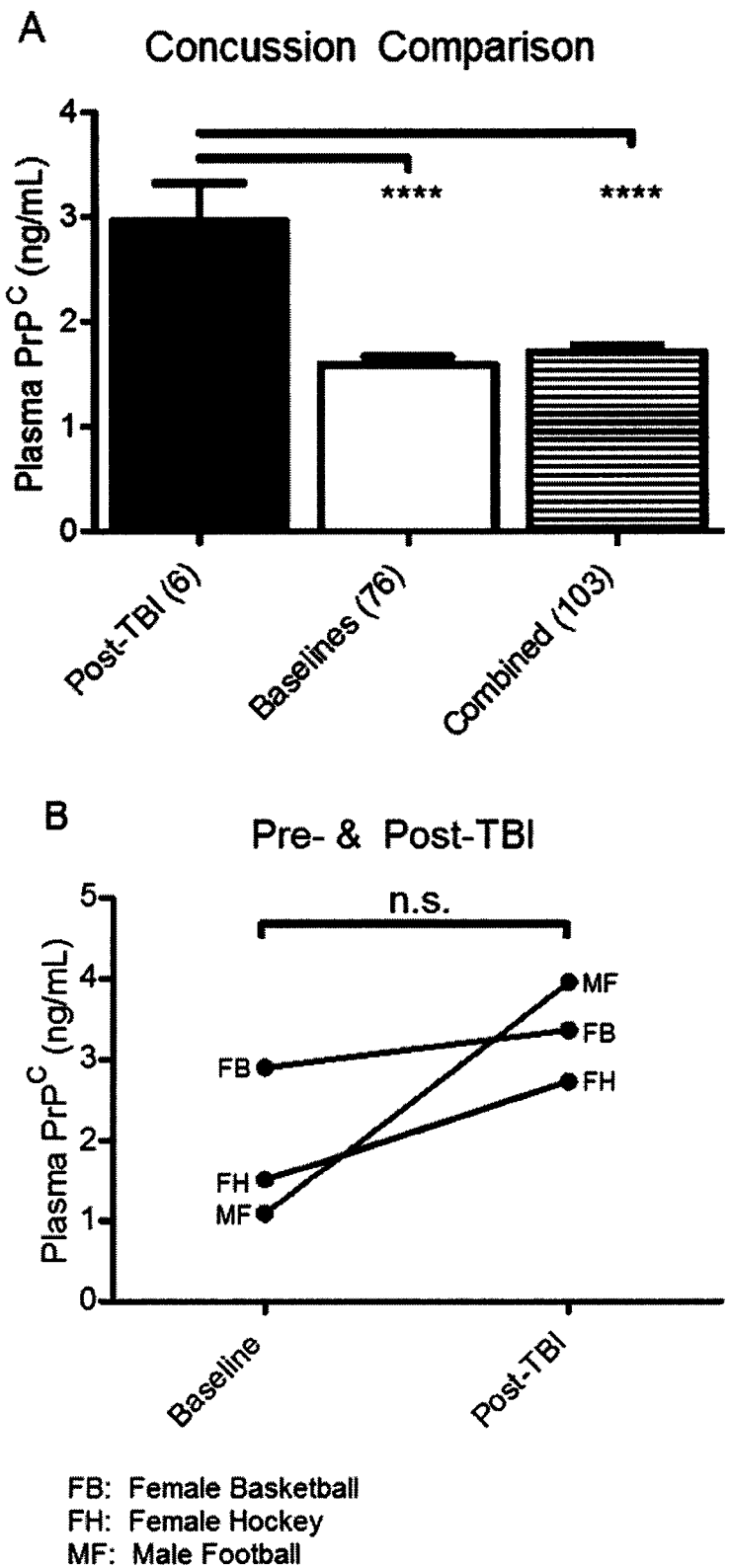
FIG. 6 shows A) two-tailed unpaired student's t-test showing post-TBI $PrP^C$ concentrations (n=6, 2.96 ng/mL±0.37 SEM) are significantly elevated compared with either offseason athlete baseline concentration (n=76, 1.59 ng/mL±0.07 SEM)(p<0.0001), or both athletes and non-athletes combined (n=103, 1.70 ng/mL±0.07 SEM) (p<0.0001). B) Two-tailed paired t-test showing there was no significant difference between three sets of of pre- and post-TBI $PrP^C$ values (p=0.1666).

Blood from six athletes who sustained concussion as assessed using the SCAT3 criteria by teams' doctors and physical therapists were collected. Depending on access to the concussive athletes, the blood samples were collected within 24 hrs to 6 days post-mTBI. During the last sport season, Huskies Athletic teams had 4 female and 2 male concussive players ranging from different sport teams including Canadian football, ice hockey, basketball and wrestling. Comparison of mean plasma PrP$^C$ in post-concussion samples (2.96 ng/mL±0.37, n=6) was found to be significantly higher (p<0.0001) than levels in baseline samples collected in the offseason (1.59 ng/mL±0.07, n=76) and against combined baselines with the normal population (1.70 ng/mL±0.07, n=103) (see FIG. 6-A). Of the 76 baseline samples collected from athlete participants during the offseason, only three individuals sustained a concussion during the season to allow pre- and post-TBI comparison (see FIG. 6-B). Although an unpaired t-test comparison showed there was no significant difference between three sets of pre- and post-TBI PrP$^C$ values, the number tested was low and did show an increasing trend in post-concussion PrP$^C$.

Discussion

Sport-related concussions are the most common cases of mTBI among children and young adults (Nobel et al., 2013; Selassie et al., 2013; Stewart et al., 2013). Despite several clinical symptoms and manifestations, it is believed that the majority of concussive events still remain unreported or ignored. Considering limitations and shortcomings of diagnostic medical imaging techniques, it is thus necessary to have access to more reliable and easy to use quantitative diagnostic concussion tests to identify concussive athletes and to reduce the risk of potential catastrophic second impact syndrome. Protein biomarkers in biological fluids have opened new horizons in TBI and concussion diagnosis. In the present study, concentrations of plasma soluble PrP$^C$ were examined in university student athletes who had a sports-related concussion (six concussion cases in the last season). It was found that the post-concussion levels of plasma soluble PrP$^C$ were significantly higher when compared with the normal plasma PrP$^C$ values in young adults.

PrP$^C$ is a loosely associated lipid raft protein known for several important physiological functions including its neuroprotective role in the brain. In this Example, it was hypothesized, that in a concussive event, the applied force on the brain may dislodge PrP$^C$ off the neuronal lipid rafts, which may eventually ending up in circulation. Therefore, the plasma soluble PrP$^C$ could be used as a potential biomarker for mTBI diagnosis. Although PrP$^C$ is prominently expressed in CNS, emerging evidence indicates that soluble PrP$^C$ could cross the blood brain barrier in a bidirectional manner (Banks et al., 2009). PrP$^C$ levels in biological fluids such as CSF and plasma have been previously used as a useful biomarker for certain pathological conditions (Krupinski et al., 2008; Meyne et al., 2009; Mitsios et al., 2007; Picard-Hagen et al., 2006; Roberts et al., 2010; Torres et al., 2012; Volkel et al., 2001). Increased plasma PrP$^C$ concentrations have been previously reported following stroke and in patients with various neurodegenerative diseases (Mitsios et al., 2007; Volkel et al., 2001). Furthermore, recent studies have shown that patients with cerebrovascular disease or vascular endothelial damage had higher levels of plasma $PrP^C$ than control values (Krupimski et al., 2008; Simak et al., 2002; Starke et al., 2002). Moreover, the role of soluble $PrP^C$, in the modulation of immune cell activation centrally and peripherally, was proposed to be used as a biomarker for neuroinflammation and encephalitis; particularly in cases related to HIV-infected individuals (Roberts et al., 2010).

Most of the above studies were conducted with older subjects, whereas the subjects studied in the present examples were young adults who were mainly involved in high contact sports. It appears that the mean plasma $PrP^C$ in healthy young individuals is lower than what has been previously reported in older population (Volkel et al., 2001; Breitling et al., 2012). The present participants varied between 18-30 years old, whereas recruited individuals in Breitling et al. study were between 72-76 years old (Breitling et al., 2012). Age-dependent expression of $PrP^C$ has been previously reported, but any significant difference across various age groups was not observed in this population (Politopoulou et al., 2000). Slightly higher (non-significant) soluble $PrP^C$ was also observed in female plasma samples when compared with that in males. Lower soluble $PrP^C$ level was observed among offseason athlete baseline values as compared with controls (non-athlete students). However, due to unequal sample sizing (76 baseline vs. 27 non-athletes), the possibility that heterogeneity of results from the normal sample group being more pronounced cannot be ruled out. The soluble $PrP^C$ is also involved in activation of immune cells and immune response (Haddon et al., 2009; Jeon et al., 2013). Thus, without wishing to be bound by theory, it is possible that the lower soluble $PrP^C$ levels in off-season athletes may be required to accommodate relatively lower pro-inflammatory cytokines condition necessary for promoting off-seasonal CNS repair. Most recently, Bazarian et al. reported similar differences in serum levels of ApoA1 and S100B autoantibody titer between off-season athletes and their controls (Bazarian et al., 2014).

According to the present results, there is indeed a significant rise of the plasma soluble $PrP^C$ in post-mTBI/concussion samples compared with both the general control young adult population and offseason athlete plasma samples. This clearly indicates that a rise in plasma $PrP^C$ is associated with sport-related concussion. However, comparison pre- and post-TBI values (for the same individuals, i.e. the three concussive persons) showed no significant difference (due to a low n of 3) when evaluated as one set of values, although there is an increasing trend in plasma $PrP^C$ levels. However, not all athletes had submitted a baseline sample during the offseason. Thus, of the six concussion samples collected the present inventor was limited to only three corresponding baselines to compare against. These pairs showed an upward trend in plasma $PrP^C$ concentration despite delayed periods in collection following injury. It has been reported that the soluble $PrP^C$ could cross the blood brain barrier in a bidirectional manner (Banks et al., 2009) and the blood brain barrier may be disrupted in some concussive events (Marchie et al., 2013). Due to the limitation in the number of concussed athletes and variation in the time period between injury and collection, which ranged between 1-6 days depending on subject availability, it cannot definitively determine whether this rise in plasma $PrP^C$ is directly attributed to protein shedding from the CNS or partly originated from circulatory blood cells following the initial injury. Recent evidence suggests that normal $PrP^C$ may be also secreted out (on exosomes) from cultured neurons following toxic challenges such as NMDA-induced excitotoxicity ((Wang et al., 2012). Moreover, $PrP^C$ containing exosomes have recently been isolated from human plasma (Ritchie et al., 2013). Since neuronal excitotoxicity plays a major role in the pathogenesis of TBI (reviewed in Algattas et al., 2014; Parsons et al., 2014), it is thus plausible to hypothesize that the CNS is a major contributor to plasma soluble $PrP^C$ following the concussion.

The goal of this Example was to determine the viability of using plasma levels of $PrP^C$ in athletes following concussion to be compared against controls as a biomarker for sports concussion. Results obtained from gender and different age groups of young adults show no significant difference which means there is no gender and age variation in human plasma $PrP^C$ concentration, making it an ideal parameter for testing as a biomarker. The results presented in this Example provide first evidence that easily accessible plasma soluble $PrP^C$ might have a relevant association with sport-related concussion/mTBI and may be a useful biomarker to identify concussive athletes at risk.

Example 4

This Example was carried out to establish age- and sex-specific reference intervals (RIs) for serum soluble $PrP^C$ concentration in healthy children measured by the modified quantitative ELISA method described herein. Results show that there is no distinctive difference between male and female concentrations, nor is there any significant alteration with age. Having pediatric RIs available for this analyte may prove to be valuable as the potential use of $PrP^C$ as a biomarker for certain conditions, such as assessing brain injury, expands to children as well.

Methods

Participant Recruitment and Sample Collection

The CALIPER initiative was approved by the Institutional Review Board at the Hospital for Sick Children (Toronto, ON, Canada). As previously described, healthy children (1 to 18 years of age) were recruited in the greater Toronto area through various community programs to ensure broad multi-ethnic participation (Colantonio et al., 2012). Sample collection was performed following informed parental consent and completion of a brief questionnaire. The exclusion criteria included history of chronic illness or metabolic disease, acute illness within the previous month, or use of prescribed medication within the previous two weeks. Serum samples were collected in a serum separator tube (SST vacutainer; BD) and were centrifuged, separated, divided into aliquots, and stored at 80° C. until analysis. Sample aliquots were transferred to the University of Saskatchewan on dry ice for $PrP^C$ content quantification.

Serum $PrP^C$ ELISA

Sensitive quantification of serum $PrP^C$ was performed using a modified commercial PrP ELISA detection kit (SpiBio A05201) as previously described (Pham et al., 2015 a & b). Briefly, the kit utilizes a double-antibody sandwich allowing for qualitative determination of $PrP^C$ in various mammalian biological fluids. For the present purposes, the manufacturer's protocol has been modified for sensitive quantification. Full length pure recombinant $PrP^C$ (Prionatis, Zurich, Switzerland; α-Rec Mouse PrP(23-231), cat. # RPA0101S) was used for producing serial protein standards (0.625-20 ng/mL) to produce the calibration curve. Diluted samples were incubated in antibody-coated wells overnight at 4° C. with shaking to ensure adequate antigen binding. Acetylcholinesterase-conjugated 'Fab antibody solution was then added and bound to captured $PrP^C$. A colorimetric reaction proportional to captured $PrP^C$ is produced using Ellman's reagent, the absorbance of which was measured at 405 nm using a spectrophotometer (Molecular Devices, LLC., SpectraMax M5, Sunnyvale Calif., USA). Sample raw absorbance values were interpolated into protein concentrations using the calibration curve.

Statistical Analysis

All statistical analyses and figures were produced using the IBM SPSS 21 and Medcalc software packages. Data were analyzed in accordance with CLSI C28-A3 guidelines as previously described (Colantonio et al., 2012). Visual inspection of the data was done through scatter and distribution plots; outliers were then removed according to Tukey's method (1.5*interquartile range) (Tukey 1977). Age- and sex-stratified partitions were determined by visually inspecting distribution and scatter plots for overall trends. The need for partitioning was statistically evaluated using Harris and Boyd's test to determine whether subgroups were statistically different to warrant being stratified (Fuentes-Arderiu et al., 1997). The non-parametric rank method [p*(n+1)] was used to calculate the RI at the 2.5- and 97.5 percentiles for sample sizes of n≥120. For partitions with sample sizes of n≥120, the robust method was used to calculate the RI (Horn et al., 1998). The 90% confidence intervals were also calculated for the RI limits. Test of normality was determined using the Shapiro-Wilks test. Student's T test was performed for comparison between mean concentration values between sexes. One way analysis of variance (ANOVA) was used for multiple comparison of mean concentration values across stratified age groups. Correlational analysis was performed to determine the potential relationship between serum $PrP^C$ concentration and age. Analyses were considered statistically significant when $p<0.05$.

Results

Normal Distribution

Figure 9:
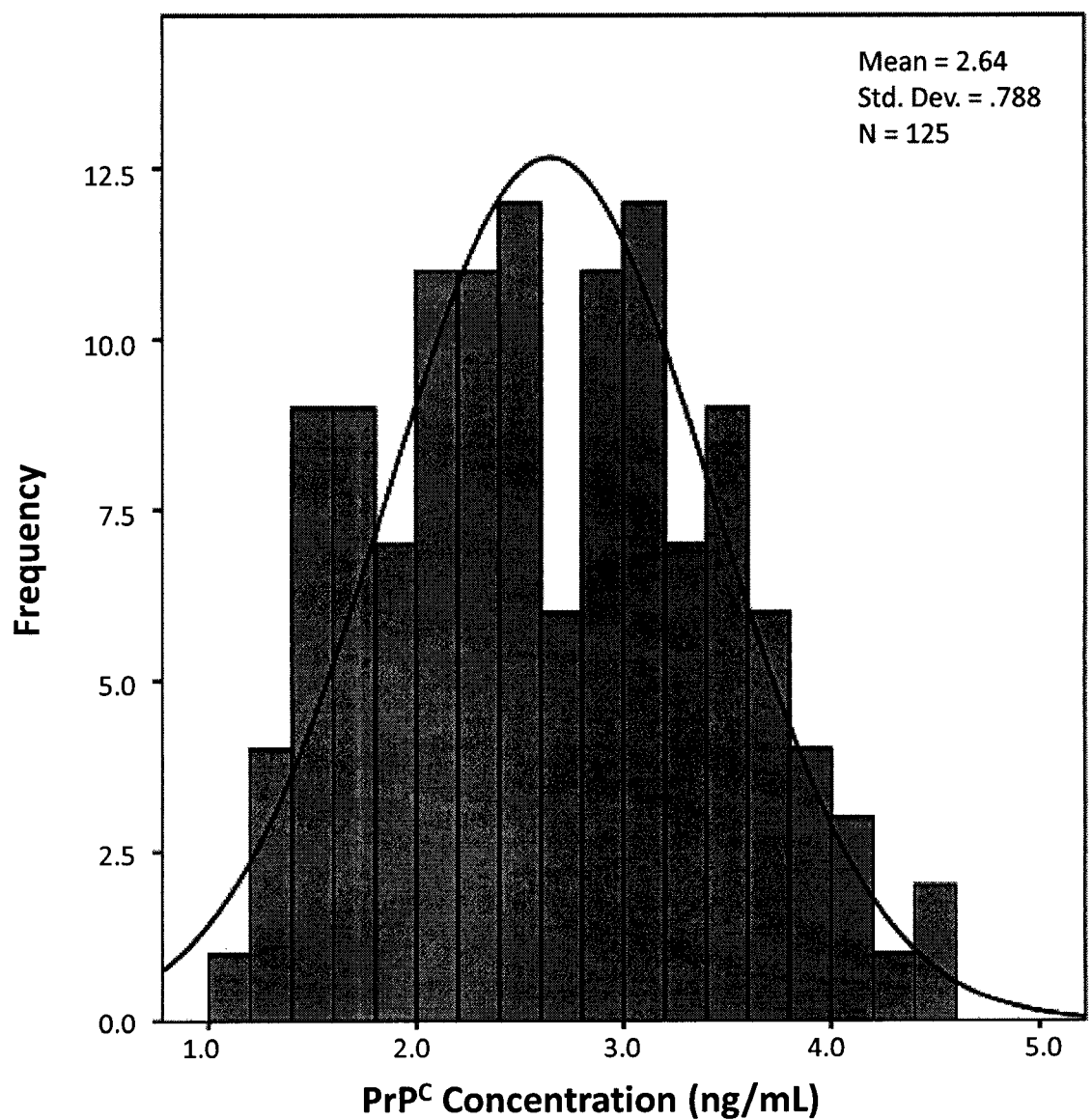
FIG. 9 shows a histogram of Gaussian distribution of $PrP^C$ concentration results.

The pooled results of pediatric serum $PrP^C$ concentration displays normal Gaussian distribution as calculated by the Shapiro-Wilks test (W=0.979, p=0.052). Analysis of distribution based on sex shows that male (W=0.9730, p=0.2205), and female (W=0.9744, p=0.181) were the same. Graphical representation of normal frequency distribution is provided in histogram and Q-Q plot (see FIG. 9).

Pediatric Reference Interval

As previously described, the lower and upper limits of the conventional 95% RI was determined by non-parametric method by calculating the corresponding data values of the rank products of 2.5- and 97.5-percentiles respectively (Jung and Adeli 2009). Thus, the limits were set as the $3^{rd}$ and $123^{rd}$ ranked values. The 90% confidence limits for the lower reference limit was determined at rank values 1 and 7, while those for the upper limit was determined at 119 and 125. In summary, the pediatric RI for serum $PrP^C$ is 1.37 (1.18-1.48) to 4.21 (3.88-4.48) ng/mL. The robust method determined RIs for males at 0.91 (0.64-1.19) to 4.29 (3.98-4.59) ng/mL, as well as females at 1.13 (0.92-1.36) to 4.17 (3.89-4.40) ng/mL.

Age and Sex Effect

Figure 10:
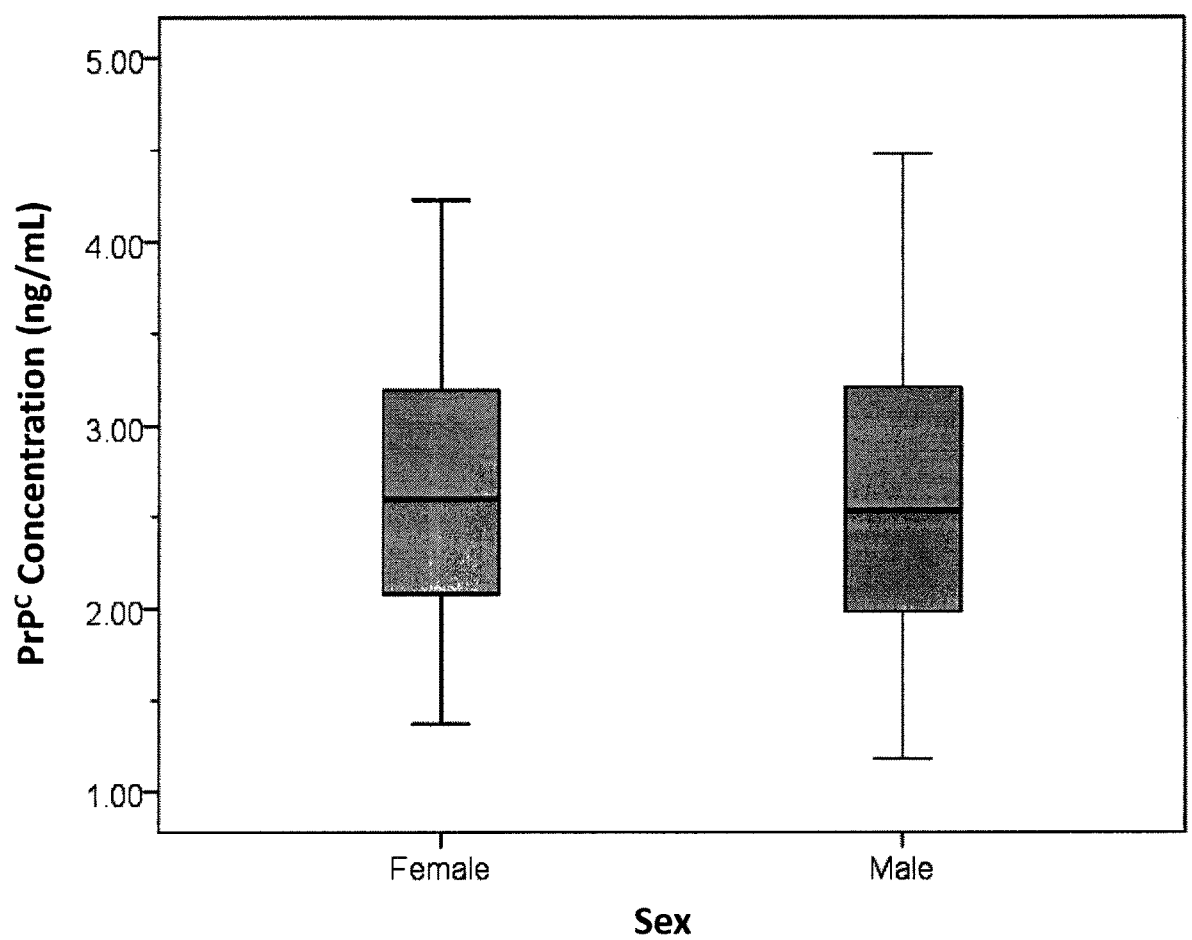
FIG. 10 shows a sex comparison of $PrP^C$ concentration between males and females. Student's unpaired T test showed no significant difference of mean $PrP^C$ concentration between males and females [mean (ng/mL)±SD; (males) 2.62±0.84 n=58; vs. (females) 2.67±0.75 n=67; p=0.739]
Figure 11:
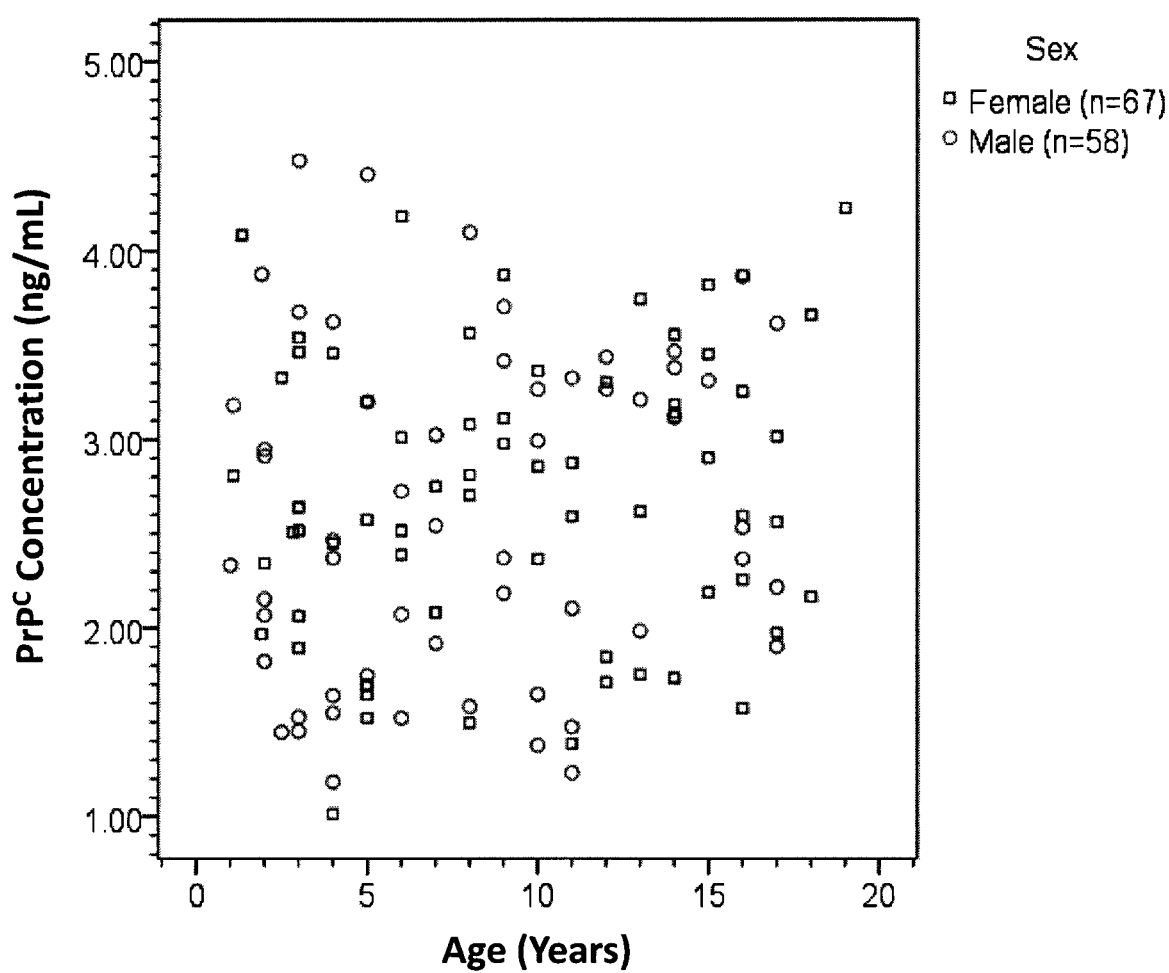
FIG. 11 shows a scatterplot analysis of $PrP^C$ with age. Graphical presentation of $PrP^C$ concentration and age. Correlational analysis shows no significant relationship with age and $PrP^C$ concentration in males (Pearson's R=0.092, p=0.493), females (R=0.122, p=0.324), or combined (R=0.110, p=0.220).

Student's unpaired T test showed no significant difference between mean $PrP^C$ concentration between males (2.62±0.84) and females (2.66±0.75) (p=0.246; see Table 8). Boxplot representation of concentration values separated by sex show both male and female data sets share similar medians and interquartile range (see FIG. 10). Correlational analysis shows no significant effect on $PrP^C$ concentration due to age as calculated by Pearson's R for males (0.092, p=0.493), females (0.122, p=0.324), and when combined (0.110, p=0.220) (see FIG. 11).

Results were also stratified into age brackets divided by two year intervals (see Table 8). However, to establish an RI a minimum sample size of 40 is typically required. Thus, the present inventor was unable to establish age-specific RIs. One-way ANOVA of age brackets shows no significant difference when analyzed by males (p=0.931), females (p=0.900), and both sexes combined (p=0.798).

Discussion

The flurry of research into biomarkers over the past decade has shown great promise in streamlining effective care measures for various conditions and even injuries. The ongoing CALIPER initiative is aimed at addressing the issue of inadequate reference values for biochemical substances in healthy children from 1 to 18 years of age. It is increasingly clear that children should not be observed in the clinical setting as small adults. Similar to how drug treatments must be tapered differently when administered in children, interpretation of biological markers should also be able to accommodate children. The exact function of $PrP^C$ is still not fully understood, but it has been suggested the protein serves important roles in the CNS required for proper functioning. As set out in the previous Examples, the present inventor has demonstrated the use of $PrP^C$ in blood as a biomarker for TBI in an animal model as well as in a preclinical study of sports concussion victims (Pham et al., 2015 a & b).

Other groups have also explored $PrP^C$'s usage as a biomarker, but the majority of such investigations have exclusively focused on older populations (Völkel et al., 2001; Roberts et al., 2010; Torres et al., 2013; Meyne et al., 2009; Krupinski et al., 2008; Mitsios et al., 2007). This is likely a result of study designs aimed towards neurodegenerative diseases or conditions, which rarely if ever affect children. Yet the rising incidence of TBI over the past decade poses a great concern that children are not exempt from degenerative long term neurological and behavioral consequences.

According to the Centers for Disease Control and Prevention, in 2010 there were approximately 2.5 million emergency department (ED) visits, hospitalizations, and deaths associated with TBI in the U.S. (CDC 2015). Every year approximately half a million (473,947) ED visits are made by children (Langlois et al., 2005). Sports and recreation-related injuries accounted for 248,418 cases of children ED visits that resulted in diagnosis of concussion or TBI. Falls account for more than half (55%) of children TBI cases, and further disconcerting is that the rate of fall-related TBI has increased 62% within the last decade. Regardless of the cause, TBI in children may have far-reaching negative consequences in terms of cognitive, behavioral, social, and potentially even motor functioning later on in life (Thurman 1990; Barlow et al., 2005). Proper clinical management and precautionary measures are essential in ensuring those who have suffered TBI recover without looming long-term impediments. However, clinicians agree that the rate of TBI-related ED visits grossly underestimates the true incidence rate when accounting for underreporting of symptoms perhaps due to a lack of awareness or fear of being forcibly excluded from participating, which is often seen amongst athletes (Fazio et al., 2007). Due to practical shortcomings and lack of sensitivity with conventional imaging techniques in detecting mTBI, for the aim of providing more objective diagnosis and timely decision making, much effort has been put towards surrogate markers in biological fluids.

Nearly 100 different biomarkers have been studied in children for TBI, but only a small proportion of which have shown promise (as reviewed in Papa et al., 2013). The main mechanistic approach towards research into TBI biomarkers is that injury may cause disruption of cell integrity, due to physical trauma or even prolonged deleterious effects such as neuroinflammation and toxicity.

Cellular contents are then released and cleared away via the brain's glymphatic system allowing their measurement in the CSF and systemic circulation (Plog et al., 2015). Furthermore, $PrP^C$'s ability to cross the blood-brain barrier (BBB) may make it a sensitive marker for mTBI, which can present without extensive BBB disruption, as opposed to other proteins (Banks et al., 2009; Blyth et al., 2009). In this report the present inventor provides the first RI for serum $PrP^C$ in children. Small blood samples from 125 children and adolescents (<18 years of age) were collected at Sick Kids Hospital (Toronto, ON, Can). The inclusion criteria required that donors were healthy without any pre-existing medical condition or disease. Using a modified commercial ELISA, serum samples were assayed in triplicate for sensitive quantification of full-length soluble $PrP^C$ content (see Table 8 for results summary). Frequency distribution of sample concentrations displayed Gaussian distribution (see FIG. 9), and showed no significant age-nor sex-dependent effects as determined by correlation analysis and t-test respectively. Therefore this protein may be used as a general marker for all children. According to CLSI C28-A3 statistical guidelines, non-parametric analysis of the RI and associated 90% confidence intervals was calculated at 1.37 (1.18-1.48) to 4.22 (3.88-4.48) ng/mL. Furthermore, the robust method calculated sex-stratified RIs for males [0.91 (0.64-1.19) to 4.29 (3.98-4.59) ng/mL] and females [1.13 (0.92-1.36) to 4.17 (3.89-4.40)]. Mean $PrP^C$ concentration for all pediatric samples is 2.64 ng/mL, which when compared to the other examples as well as other reports from older populations suggests a potential decline later in life (Pham et al., 2015a; Krupinski et al., 2008; Mitsios et al., 2007). ELISA validation intra-assay and inter-assay confidence values were determined at 5.2% and 5.3% respectively.

While the present disclosure has been described with reference to what are presently considered to be the examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Mann-Whitney U Test for Net: Control (n = 9) vs. net (n = 15).

Descriptive Statistics

| | | | | | | Percentiles | | |
| --- | --- | --- | --- | --- | --- | --- | --- | --- |
| | N | Mean | Std. Deviation | Minimum | Maximum | 25th | 50th (Median) | 75th |
| Net | 24 | 6.6970 | 1.51091 | 3.99 | 9.99 | 5.7979 | 6.4387 | 7.6194 |
| Groups | 24 | 1.63 | .495 | 1 | 2 | 1.00 | 2.00 | 2.00 |

Ranks

| | Groups | N | Mean Rank | Sum of Ranks |
| --- | --- | --- | --- | --- |
| Net | 1 | 9 | 12.22 | 110.00 |
| | 2 | 15 | 12.67 | 190.00 |
| | Total | 24 | | |

Test Statistics[b]

| | Net |
| --- | --- |
| Mann-Whitney U | 65.000 |
| Wilcoxon W | 110.000 |
| Z | −.149 |
| Asymp. Sig. (2-tailed) | .881 |
| Exact Sig. [2*(1-tailed Sig.)] | .907[a] |

[a]Not corrected for ties.
[b]Grouping Variable: Groups

TABLE 2

Mann-Whitney U test for Restraint: control (n = 9) vs. restraint (n = 12).

Descriptive Statistics

| | | | | | | Percentiles | | |
| --- | --- | --- | --- | --- | --- | --- | --- | --- |
| | N | Mean | Std. Deviation | Minimum | Maximum | 25th | 50th (Median) | 75th |
| Prion Concentration | 21 | 7.4839 | 1.64451 | 3.99 | 10.63 | 6.3111 | 7.6605 | 9.5495 |
| Restraint | 21 | 1.57 | .507 | 1 | 2 | 1.00 | 2.00 | 2.00 |

TABLE 2-continued

Mann-Whitney U test for Restraint: control (n = 9) vs. restraint (n = 12).

Ranks

| | Restraint | N | Mean Rank | Sum of Ranks |
|---|---|---|---|---|
| Prion Concentration | 1 | 9 | 7.67 | 69.00 |
| | 2 | 12 | 13.50 | 162.00 |
| | Total | 21 | | |

Test Statistics[b]

| | Prion Concentration |
|---|---|
| Mann-Whitney U | 24.000 |
| Wilcoxon W | 69.000 |
| Z | −2.132 |
| Asymp. Sig. (2-tailed) | .033 |
| Exact Sig.[2*(1-tailed Sig.)] | .034[a] |

[a]Not corrected for ties.
[b]Grouping Variable: Restraint

TABLE 3

Mann-Whitney U Test for Whiplash: Control (n = 9) vs. whiplash (n = 11)

Descriptive Statistics

| | N | Mean | Std. Deviation | Minimum | Maximum | 25th | 50th (Median) | 75th |
|---|---|---|---|---|---|---|---|---|
| Whiplash | 20 | 7.9908 | 1.90403 | 3.99 | 11.16 | 6.4692 | 8.2906 | 9.3011 |
| Groups | 20 | 1.55 | .510 | 1 | 2 | 1.00 | 2.00 | 2.00 |

Ranks

| | Groups | N | Mean Rank | Sum of Ranks |
|---|---|---|---|---|
| Whiplash | 1 | 9 | 6.11 | 55.00 |
| | 2 | 11 | 14.09 | 155.00 |
| | Total | 20 | | |

Test Statistics[b]

| | Whiplash |
|---|---|
| Mann-Whitney U | 10.000 |
| Wilcoxon W | 55.000 |
| Z | −3.001 |
| Asymp. Sig. (2-tailed) | .003 |
| Exact Sig. [2*(1-tailed Sig.)] | .002[a] |

[a]Not corrected for ties.
[b]Grouping Variable: Groups

TABLE 4

Student T test for Overall Treatment: Control (n = 9) vs. Three treatment groups - net, restraint and whiplash (n = 38).

Group Statistics

| | Groups | N | Mean | Std. Deviation | Std. Error Mean |
|---|---|---|---|---|---|
| Treatment | 1 | 9 | 6.6001 | 1.46146 | .48715 |
| | 2 | 38 | 7.8817 | 1.77909 | .28861 |

TABLE 4-continued

Student T test for Overall Treatment: Control (n = 9) vs. Three treatment groups - net, restraint and whiplash (n = 38).

Independent Samples Test

| | | Levene's Test for Equality of Variances | | t-test for Equality of Means | | | | | 95% Confidence Interval of the Difference | |
|---|---|---|---|---|---|---|---|---|---|---|
| | | F | Sig. | t | df | Sig. (2-tailed) | Mean Difference | Std. Error Difference | Lower | Upper |
| Treatment | Equal variances assumed | .772 | .384 | −2.002 | 45 | .051 | −1.28158 | .64018 | −2.57097 | .00780 |
| | Equal variances not assumed | | | −2.283 | 14.222 | .040 | −1.28158 | .56623 | −2.49424 | .06893 |

TABLE 5

Pearson Correlation of PSI and Prion Concentration

Correlations

| | | Prion Concentration | PSI |
|---|---|---|---|
| Prion Concentration | Pearson Correlation | 1 | .151 |
| | Sig. (2-tailed) | | .311 |
| | N | 47 | 47 |
| PSI | Pearson Correlation | .151 | 1 |
| | Sig. (2-tailed) | .311 | |
| | N | 47 | 47 |

TABLE 6

Participant Summary

| | n | Age (years) | | | $PrP^C$ Concentration (ng/mL) | | |
|---|---|---|---|---|---|---|---|
| | | Mean ± SD | Median | Range | Mean ± SEM | Median | Range |
| Non-Athlete | 27 | 24.48 ± 2.99 | 24.00 | 18-30 | 2.02 ± 0.15 | 2.23 | 0.72-3.87 |
| Male | 15 | 24.67 ± 1.76 | 24.00 | 22-29 | 2.12 ± 0.18 | 2.32 | 1.11-3.41 |
| Female | 12 | 24.25 ± 4.14 | 23.50 | 18-30 | 1.89 ± 0.27 | 2.27 | 0.72-3.87 |
| Athlete | 76 | 20.04 ± 1.84 | 20.00 | 18-26 | 1.59 ± 0.64 | 1.51 | 0.56-3.66 |
| Male | 39 | 20.41 ± 1.92 | 20.00 | 18-24 | 1.44 ± 0.10 | 1.34 | 0.56-3.17 |
| Female | 37 | 19.65 ± 1.70 | 19.00 | 18-26 | 1.75 ± 0.10 | 1.59 | 1.05-3.66 |
| Combined | 103 | 21.20 ± 2.94 | 21.00 | 18-30 | 1.70 ± 0.07 | 1.55 | 0.56-3.87 |
| Male | 54 | 21.59 ± 2.67 | 22.00 | 18-29 | 1.63 ± 0.10 | 1.40 | 0.56-3.41 |
| Female | 49 | 20.78 ± 3.18 | 20.00 | 18-30 | 1.79 ± 0.10 | 1.62 | 0.72-3.87 |

SD = Standard Deviation
SEM = Standard Error of the Mean

TABLE 7

Plasma $PrP^C$ ELISA Results Summary
$PrP^C$ Concentration (ng/mL)

| Group | Target Pressure (PSI) | Actual Pressure (PSI) | n | Mean ± S.E. | Median | Range |
|---|---|---|---|---|---|---|
| Sham Control | 0 | 0 | 19 | 2.46 ± 0.14 | 2.66 | 0.67-3.35 |
| Blast | 15 | 15 ± 0.2 | 7 | 3.74 ± 0.34 | 3.99 | 2.10-4.67 |
| | 20 | 20 ± 0.8 | 7 | 4.27 ± 0.26 | 4.47 | 3.27-5.34 |
| | 25 | 25 ± 0.3 | 12 | 4.18 ± 0.18 | 4.26 | 3.06-5.37 |
| | 30 | 30 ± 0.9 | 7 | 3.54 ± 0.30 | 3.25 | 2.68-4.84 |
| | 15-30 | | 33 | 3.97 ± 0.13 | 4.19 | 2.10-5.37 |

S.E. = Standard Error

Blood plasma from control (N = 19, 0 PSI) and blast (n = 33, 15-30 PSI) group rats were assayed using a modified commercial $PrP^C$ ELISA kit for quantification. Individual results not provided.

TABLE 8

$PrP^C$ concentrations results listed by sex and age

| Sex | N | $PrP^C$ Concentration (ng/mL) | | |
|---|---|---|---|---|
| | | Mean | Median | Min-Max |
| Male | 58 | 2.62 ± 0.84 | 2.54 | 1.18-4.48 |
| Female | 67 | 2.66 ± 0.75 | 2.59 | 1.37-4.22 |
| Age | N (males, females) | | | |
| ≤2 | 12 (8, 4) | 2.71 ± 0.70 | 2.38 | 1.97-4.08 |
| 2-4 | 22 (11, 11) | 2.51 ± 0.92 | 2.46 | 1.18-4.48 |
| 4-6 | 16 (6, 10) | 2.51 ± 0.91 | 2.45 | 1.52-4.40 |
| 6-8 | 14 (6, 8) | 2.61 ± 0.73 | 2.68 | 1.50-4.10 |
| 8-10 | 14 (8, 6) | 2.74 ± 0.73 | 2.90 | 1.38-3.87 |
| 10-12 | 12 (6, 6) | 2.40 ± 0.80 | 2.54 | 1.23-3.32 |
| 12-14 | 13 (6, 7) | 2.88 ± 0.68 | 3.13 | 1.73-3.74 |
| 14-16 | 13 (4, 9) | 2.84 ± 0.68 | 2.84 | 1.58-3.87 |
| 16-18 | 9 (3, 6) | 2.75 ± 0.89 | 2.22 | 1.88-4.22 |
| Total | 125 (58, 67) | 2.64 ± 0.79 | 2.59 | 1.18-4.48 |

TABLE OF SEQUENCES

| SEQ ID NO | SEQUENCE | DESCRIPTION |
|---|---|---|
| 1 | DYEDRYYREN | Human amino acid sequence |
| 2 | PQGGGGWGQPHGGGWGQPHGGG WGQPHGGGWGQPHGGGWGQ | Human amino acid sequence |

REFERENCES

Anderson, R. E., Hansson, L. O., Nilsson, O., Dijlai-Merzoug, R., and Settergren, G. (2001). High serum S100B levels for trauma patients without head injuries. Neurosurgery 48, 1255-1258.

Agoston, D. V., Gyorgy, A., Eidelman, O., and Pollard, H. B. (2009). Proteomic biomarkers for blast neurotrauma: targeting cerebral edema, inflammation, and neuronal death cascades. J. Neurotrauma 26, 901-911.

Agoston, D. V., and Elsayed, M. (2012). Serum-based protein biomarkers in blast-induced traumatic brain injury spectrum disorder. Front. Neurol. 3, 1-10.

Aguzzi A, Calella A M (2009) Prions: protein aggregation and infectious diseases. Physiol Rev 89: 1105-1152.

Aguzzi A, Polymenidou M. Mammalian prion biology: one century of evolving concepts. Cell 2004; 116(2): 313-27

Algattas H, Huang J H (2014) Traumatic Brain Injury pathophysiology and treatments: early, intermediate, and late phases post-injury. Int J Mol Sci 15: 309-341.

Alvarez L. War veterans' concussions are often overlooked. New York Times. Aug. 25, 2008: A1

Banks W A, Robinson S M, Diaz-Espinoza R, Urayama A, Soto C (2009) Transport of prion protein across the blood-brain barrier. Exp Neurol 218: 162-167. Barkhoudarian G, Hovda D A, Giza C C (2011) The molecular pathophysiology of concussive brain injury. Clin Sports Med 30: 33-48, vii-iii.

Barlow K M, Thomson E, Johnson D, Minns R A. Late neurologic and cognitive sequelae of inflicted traumatic brain injury in infancy. Pediatrics. 2005; 116(2):e174-85.

Bauman R A, Ling G, Tong L, et al. An introductory characterization of a combat-casualty-care relevant swine model of closed head injury resulting from exposure to explosive blast. J Neurotrauma 2009; 26: 841-60

Bazarian J J, Zhu T, Zhong J, Janigro D, Rozen E, et al. (2014) Persistent, Long-term Cerebral White Matter Changes after Sports-Related Repetitive Head Impacts. PLoS One 9: e94734.

Belanger H G, Vanderploeg R D, Curtiss G, Warden D L (2007) Recent neuroimaging techniques in mild traumatic brain injury. J Neuropsychiatry Clin Neurosci 19: 5-20.

Bendheim P E, Brown H R, Rudelli R D, et al. Nearly ubiquitous tissue distribution of the scrapie agent precursor protein. Neurology 1992; 42: 149-56

Blyth B J, Farhavar A, Gee C, Hawthorn B, He H, Nayak A, et al. Validation of serum markers for blood-brain barrier disruption in traumatic brain injury. J Neurotrauma. 2009; 26(9):1497-507.

Boden B P, Tacchetti R L, Cantu R C, Knowles S B, Mueller F O (2007) Catastrophic head injuries in high school and college football players. Am J Sports Med 35: 1075-1081.

Breitling L P, Muller H, Stegmaier C, Kliegel M, Brenner H (2012) Association of prion protein with cognitive functioning in humans. Exp Gerontol 47: 919-924.

Brookings Institution, Saban Center for Middle East Policy. Iraq index: tracking variables of reconstruction and security in post-Saddam Iraq. Apr. 27, 2010

Caffey J. On the theory and practice of shaking infants: Its potential residual effects of permanent brain damage and mental retardation. American Journal of Diseases of Children 1972; 124(2): 161-9

Center for Disease Control and Prevention. 2012. Injury Prevention & Control: Traumatic Brain Injury, retrieved Apr. 16, 2013 from, http://www.cdc.gov/traumaticbraininjury/

Chavko M, Koller W A, Prusaczyk W K, et al. Measurement of blast wave by a miniature fiber optic pressure transducer in the rat brain. J Neurosci Methods 2007; 159: 277-81

Colantonio D A, Kyriakopoulou L, Chan M K, Daly C H, Brinc D, Venner A A, et al. Closing the gaps in pediatric laboratory reference intervals: a CALIPER database of 40 biochemical markers in a healthy and multiethnic population of children. Clinical chemistry. 2012; 58(5):854-68.

Cole et al. The EBV-Hybridoma Technique and its Application to Human Lung Cancer" in "Monoclonal Antibodies in Cancer Therapy", Allen R. Bliss, Inc. (1985), pages 77-96.

Daneshvar D H, Nowinski C J, McKee A C, Cantu R C (2011) The epidemiology of sport-related concussion. Clin Sports Med 30: 1-17, vii.

DeKosky, S. T., Ikonomovic, M. D., and Gandy, S. (2010). Traumatic brain injury-football, warfare, and long-term effects. N. Engl. J. Med. 14, 1293-1296.

Elder G A, Mitsis E M, Ahlers S T, Cristian A. Blast-induced mild traumatic brain injury. Psychiatr Clin N Am 2010; 33: 757-81

Fazio V C, Lovell M R, Pardini J E, Collins M W. The relation between post concussion symptoms and neurocognitive performance in concussed athletes. NeuroRehabilitation. 2007; 22(3):207-16.

Forde C T, Karri S K, Young A M, Ogilvy C S (2014) Predictive markers in traumatic brain injury: opportunities for a serum biosignature. Br J Neurosurg 28: 8-15.

Fuentes-Arderiu X, Ferre-Masferrer M, Alvarez-Funes V. Harris & Boyd's test for partitioning the reference values. European journal of clinical chemistry and clinical biochemistry: journal of the Forum of European Clinical Chemistry Societies. 1997; 35(9):733.

Gavett B E, Stern R A, McKee A C (2011) Chronic traumatic encephalopathy: a potential late effect of sport-related concussive and subconcussive head trauma. Clin Sports Med 30: 179-188, xi.

Guingab-Cagmat J D, Cagmat E B, Hayes R L, Anagli J (2013) Integration of proteomics, bioinformatics, and systems biology in traumatic brain injury biomarker discovery. Front Neurol 4: 61.

Guskiewicz K M, Register-Mihalik J, McCrory P, McCrea M, Johnston K, et al. (2013) Evidence-based approach to revising the SCAT2: introducing the SCAT3. Br J Sports Med 47: 289-293.

Haddon D J, Hughes M R, Antignano F, Westaway D, Cashman N R, et al. (2009) Prion protein expression and release by mast cells after activation. J Infect Dis 200: 827-831.

Halstead M E, Walter K D (2010) American Academy of Pediatrics. Clinical report—sport—related concussion in children and adolescents. Pediatrics 126: 597-615.

Harmon K G, Drezner J, Gammons M, Guskiewicz K, Halstead M, et al. (2013) American Medical Society for Sports Medicine position statement: concussion in sport. Clin J Sport Med 23: 1-18.

Harpio, R., and Einarsson, R. (2004). S100 proteins as cancer biomarkers with focus on S100B in malignant melanoma. Clin. Biochem. 37, 512-528.

Hoge C W, McGurk D, Thomas J L, et al. Mild traumatic brain injury in U.S. soldiers returning from Iraq. N Engl J Med 2008; 358:453-6

Horn P S, Pesce A J, Copeland B E. A robust approach to reference interval estimation and evaluation. Clinical chemistry. 1998; 44(3):622-31.

Hoshino, S., Inoue, K., Yokoyama, T., Kobayashi, S., Asakura, T., Teramoto, A., and Itohara, S. (2003). Prions prevent brain damage after experimental brain injury: a preliminary report. Acta Neurochir. S86, 297-299.

Huse W D, Sastry L, Iverson S A, et al. Generation of a large combinatorial library of the immunoglobulin repertoire in phage lambda. Science. 1989; 246: 1275-81.

Jeter C B, Hergenroeder G W, Hylin M J, Redell J B, Moore A N, et al. (2013) Biomarkers for the diagnosis and prognosis of mild traumatic brain injury/concussion. J Neurotrauma 30: 657-670.

Jeon J W, Park B C, Jung J G, Jang Y S, Shin E C, et al. (2013) The Soluble Form of the Cellular Prion Protein Enhances Phagocytic Activity and Cytokine Production by Human Monocytes Via Activation of ERK and NF-kappaB. Immune Netw 13: 148-156.

Johnson, V. E., Stewart, J. E., Begbie, F. D., Trojanowski, J. Q., Smith, D. H., and Stewart, W. (2013). Inflammation and white matter degeneration persist for years after a single traumatic brain injury. Brain 136, 28-42

Jung B, Adeli K. Clinical laboratory reference intervals in pediatrics: the CALIPERinitiative. Clinical biochemistry. 2009; 42(16-17):1589-99.

Köhler G, Milstein C. Continuous cultures of fused cells secreting antibody of predefined specificity. Nature 256, 495-497 (7 Aug. 1975).

Kozbor D, Roder J C. The production of monoclonal antibodies from human lymphocytes. Immunology Today [1983, 4(3):72-79].

Krupinski J, Turu M M, Luque A, Badimon L, Slevin M (2008) Increased PrP$^C$ expression correlates with endoglin (CD105) positive microvessels in advanced carotid lesions. Acta Neuropathol 116: 537-545.

Kuwahara C, Takeuchi A M, Nishimura T, Haraguchi K, et al. Prions prevent neuronal cell-line death. Nature 1999; 400: 255-6

Langlois J A, Rutland-Brown W, Wald M M (2006) The epidemiology and impact of traumatic brain injury: a brief overview. J Head Trauma Rehabil 21: 375-378.

Leibovici D, Gofrit O N, Stein M, et al. Blast injuries: bus versus open-air bombings—a comparative study of injuries in survivors of open-air versus confined-space explosions. J Trauma 1996; 41:1030-35

Marchi N, Bazarian J J, Puvenna V, Janigro M, Ghosh C, et al. (2013) Consequences of repeated blood-brain barrier disruption in football players. PLoS One 8: e56805.

McCafferty J, Jackson R H, Chiswell D J. Phage-enzymes: expression and affinity chromatography of functional alkaline phosphatase on the surface of bacteriophage. Protein Eng. 1991; 8: 955-61

McKee A C, Daneshvar D H, Alvarez V E, Stein T D (2014) The neuropathology of sport. Acta Neuropathol 127: 29-51.

McLennan N F, Brennan P M, McNeil A, Davies I, et al. Prion protein accumulation and neuroprotection in hypoxic brain damage. Am J Pathol 2004; 165: 227-35

Meehan W P, 3rd, Micheli L J (2011) Concussion results in deficits in neurocognitive functioning. Preface. Clin Sports Med 30: xvii-iii.

Meehan W P, 3rd, Mannix R C, O'Brien M J, Collins M W (2013) The prevalence of undiagnosed concussions in athletes. Clin J Sport Med 23: 339-342.

Metting, Z., Wilczak, N., Rodiger, L. A., Schaaf, J. M., and van der Naalt, J. (2012). GFAP and S100B in the acute phase of mild traumatic brain injury. Neurology 78, 1428-1433.

Meyne F, Gloeckner S F, Ciesielczyk B, Heinemann U, Krasnianski A, et al. (2009) Total prion protein levels in the cerebrospinal fluid are reduced in patients with various neurological disorders. J Alzheimers Dis 17: 863-873.

Milhavet, O., McMahon, H. E. M., Rachidi, W., Nishida, N., Katamine, S., Mange, A., Arlotto, M., Casanova, D., Riondel, J., Favier, A., and Lehmann, S. (2000) Prion infection impairs the cellular response to oxidative stress. Proc. Natl. Acad. Sci. U.S.A. 97, 13,937-13,942.

Mitsios N, Saka M, Krupinski J, Pennucci R, Sanfeliu C, et al. (2007) Cellular prion protein is increased in the plasma and peri-infarcted brain tissue after acute stroke. J Neurosci Res 85: 602-611.

Mitteregger G, Vosko M, Krebs B, et al. (2007) The role of the octarepeat region in neuroprotective funciton of the cellular prion protein. Brain Pathol 17: 174-83

Moser M, Colello R J, Pott U, Oesch B. (1995) Developmental expression of the prion protein gene in glial cells. Neuron 14: 509-17

Noble J M, Hesdorffer D C (2013) Sport-related concussions: a review of epidemiology, challenges in diagnosis, and potential risk factors. Neuropsychol Rev 23: 273-284.

Okie, S. (2005) Traumatic brain injury in the war zone. N. Engl. J. Med. 352, 2043-2047.

Papa L, Ramia M M, Kelly J M, Burks S S, Pawlowicz A, Berger R P. Systematic review of clinical research on biomarkers for pediatric traumatic brain injury. J Neurotrauma. 2013; 30(5):324-38.

Parsons M P, Raymond L A (2014) Extrasynaptic NMDA Receptor Involvement in Central Nervous System Disorders. Neuron 82: 279-293.

Pham N, Akonasu H, Shishkin R, Taghibiglou C. Plasma soluble prion protein, a potential biomarker for sport-related concussions: a pilot study. PLoS One. 2015; 10(2):e0117286.

Pham N, Sawyer T W, Wang Y, Jazii F R, Vair C, Taghibiglou C. Primary blast-induced traumatic brain injury in rats leads to increased prion protein in plasma: a potential biomarker for blast-induced traumatic brain injury. J Neurotrauma. 2015; 32(1):58-65.

Picard-Hagen N, Gayrard V, Viguie C, Moudjou M, Imbs C, et al. (2006) Prion protein in the cerebrospinal fluid of healthy and naturally scrapie-affected sheep. J Gen Virol 87: 3723-3727.

Plog B A, Dashnaw M L, Hitomi E, Peng W, Liao Y, Lou N, et al. Biomarkers of Traumatic Injury Are Transported from Brain to Blood via the Glymphatic System. The Journal of neuroscience. 2015; 35(2):518-26.

Politopoulou G, Seebach J D, Schmugge M, Schwarz H P, Aguzzi A (2000) Age-related expression of the cellular prion protein in human peripheral blood leukocytes. Haematologica 85: 580-587.

Rangel, A., Burgaya, F., Gavin, R., Soriano, E., Aguzzi, A., and del Rio, J. A. (2007). Enhanced susceptibility of Prnp-deficient mice to kainite-induced seizures, neuronal apoptosis, and death: Role of AMPA/kainite receptors. J. Neurosci. Res. 85, 2741-2755.

Regan T. Report: High survival rate for US troops wounded in Iraq. Christian Science Monitor Nov. 29, 2004

Ritchie A J, Crawford D M, Ferguson D J, Burthem J, Roberts D J (2013) Normal prion protein is expressed on exosomes isolated from human plasma. Br J Haematol 163: 678-680.

Ritzel, D. V., Parks, S. A., Roseveare, J., Rude, G., and Sawyer T. W. (2011). Experimental Blast Simulation for Injury Studies. NATO HFM 207: Halifax.

Rosenfeld, J. V., McFarlane, A. C., Bragge, P., Armonda, R. A., Grimes, J. B., and Ling, G. S. (2013). Blast-related traumatic brain injury. Lancet Neurol. 12, 882-893.

Roberts T K, Eugenin E A, Morgello S, Clements J E, Zink M C, et al. (2010) PrP$^C$, the cellular isoform of the human prion protein, is a novel biomarker of HIV-associated neurocognitive impairment and mediates neuroinflammation. Am J Pathol 177: 1848-1860.

Sales N, Rodolfo K, Hassig R, et al. Cellular prion protein localization in rodent and primate brain. Eur J Neurosci 1998; 10: 2464-71

Savola, O., Pyhtinen, J., Leino, T. K., Siitonen, S., Niemela, O., and Hillbom, M. (2004). Effects of head and extracranial injuries on serum protein S100B levels in trauma patients. J. Trauma 56, 1229-1234.

Schardin H. The physical principles of the effects of a detonation. German aviation medicine, World War II. Washington D.C.: Department of the US Air Force. Office of the Surgeon General; 1950: 1207-24

Selassie A W, Wilson D A, Pickelsimer E E, Voronca D C, Williams N R, et al. (2013) Incidence of sport-related traumatic brain injury and risk factors of severity: a population-based epidemiologic study. Ann Epidemiol 23: 750-756.

Shmerling D, Hegyi I, Fischer M, et al. Expression of amino-terminally truncated PrP in the mouse leading to ataxia and specific cerebellar lesions. Cell 1998; 93(2): 203-14

Shyu W C, Lin S Z, Chiang M F, Ding D C, Li K W, Chen S F, Yang H I, Li H. Overexpression of PrP$^C$ by adenovirus-mediated gene targeting reduces ischemic injury in a stroke rat model. J Neurosci 2005; 25(39): 8967-77

Sidaros, A., Skimminge, A., Liptrot, M. G., Sidaros, K., Engberg, A. W. Herning, M., Paulson, O. B., Jernigan, T. L., and Rostrup, E. (2009). Long-term global and regional brain volume changes following severe traumatic brain injury: A longitudinal study with clinical correlates. NeuroImage 44, 1-8.

Simak J, Holada K, D'Agnillo F, Janota J, Vostal J G (2002) Cellular prion protein is expressed on endothelial cells and is released during apoptosis on membrane microparticles found in human plasma. Transfusion 42: 334-342.

Small, G. W., Kepe, V., Siddarth, P., Ercoli, L. M., Merrill, D. A., Donoghue, N., Bookheimer, S. Y., Martinez, J., Omalu, B., Bailes, J., and Barrio, J. R. (2013). PET scanning of brain TAU in retired national football league players: preliminary findings. Am. J. Geriatr. Psychol. 2, 138-144.

Smith, D. H., Uryu, K., Saatman, K. E., Trojanowski, J. Q., and McIntosh, T. K. (2003). Protein accumulation in traumatic brain injury. Neuromolecular Med. 4, 59-72.

Spudich A, Frigg R, Kilic E, et al. Aggravation of ischemic brain injury by prion protein deficiency: role of ERK-1/-2 and STAT-1. Neurobiol Dis 2005; 20: 442-9

Starke R, Drummond O, MacGregor I, Biggerstaff J, Gale R, et al. (2002) The expression of prion protein by endothelial cells: a source of the plasma form of prion protein? Br J Haematol 119: 863-873.

Stern, R. A., Riley, D. O., Daneshvar, D. H., Nowinski, C. J., Cantu, R. C., and McKee, A. C. (2011). Long-term consequences of repetitive brain trauma: chronic traumatic encephalopathy. Am. Acad of Phys. Med. Rehabil. 3, S460-S467.

Stewart T C, Gilliland J, Fraser D D (2013) An epidemiologic profile of pediatric concussions: identifying urban and rural differences. J Trauma Acute Care Surg 76: 736-742.

Strathmann F G, Schulte S, Goerl K, Petron D J Blood-based biomarkers for traumatic brain injury: Evaluation of research approaches, available methods and potential utility from the clinician and clinical laboratory perspectives. Clin Biochem. 2014 Epub ahead of print.

Taghibiglou, C., Lu, J., Mackenzie, I. R., Wang, Y. T., and Cashman, N. R. (2011). Sterol regulatory element binding protein-1 (SREBP1) activation in motor neurons in excitotoxicity and amylotrophic lateral sclerosis (ALS): Indip, a potential therapeutic peptide. Biochem. Biophys. Res. Commun. 413, 159-163.

Tanielian T, Jaycox L H. Invisible wonds of war: Psychological and cognitive injuries, their consequences and services to assist recovery. Rand Corp, MG 720-CCF, Santa Monica, C A Thurman D J. The Epidemiology of Traumatic Brain Injury in Children and Youths: AReview of Research Since 1990. J Child Neurol.

Torres M, Cartier L, Matamala J M, Hernandez N, Woehlbier U, et al. (2012) Altered Prion protein expression pattern in CSF as a biomarker for Creutzfeldt-Jakob disease. PLoS One 7: e36159.

Tukey J W. Some thoughts on clinical trials, especially problems of multiplicity. Science. 1977; 198(4318):679-84.

Unden, J., Beliner, J., Ailing, C., Ingebrigtsen, T., and Rommer, B. (2005). Raised serum S100B levels after acute bone fractures without cerebral injury. J. Trauma 58, 59-61.

Uryu, K., Giasson, B. I., Longhi, L., Martinez, D., Murray, I., Conte, V., Nakamura, M., Saatman, K., Talbot, K., Horiguchi, T., McIntosh, T., Lee, V. M. Y., and Trojanowski, J. Q. (2003). Age-dependent synuclein pathology following traumatic brain injury in mice. Exp. Neurol. 184, 214-224.

Volkel D, Zimmermann K, Zerr I, Bodemer M, Lindner T, et al. (2001) Immunochemical determination of cellular prion protein in plasma from healthy subjects and patients with sporadic CJD or other neurologic diseases. Transfusion 41: 441-448.

Walz R, Amaral O B, Rockenbach I C, et al. Increased sensitivity to seizures in mice lacking cellular prion protein. Epilepsia 1999; 40: 1679-82

Wang K K, Zoltewicz J S, Chiu A, Zhang Z, Rubenstein R (2012) Release of Full-Length PrP(C) from Cultured Neurons Following Neurotoxic Challenges. Front Neurol 3: 147.

Ward R L, Clark M A, Lees J, Hawkins N J, Retrieval of human antibodies from phage-display libraries using enzymatic cleavage. J Immunol Methods. 1996; 189: 73-82. Warden D. Military TBI during the Iraq and Afghanistan wars. J Head Trauma Rehabil 2006; 21: 398-402

Warden, D. (2006). Military TBI during the Iraq and Afghanistan wars. J. Head Trauma Rehabil. 21, 398-402.

Weise J, Crome O, Sandau R, Schulz-Schaeffer W, Bahr M, Zerr I. Upregulation of cellular prion protein (PrP$^C$) after focal cerebral ischaemia and influence of lesion severity. Neurosci Lett 2004; 372: 146-150

Weise J, Sandau R, Schwarting S, et al. Deletion of cellular prion protein results in reduced Akt activation, enhanced post-ischemic caspase-3 activation, and exacerbation of ischemic brain injury. Stroke 2006; 37: 1296-1300 Wolf S J, Bebarta V S, Bonnett C J, Pons P T, Cantrill S V. Blast injuries. The Lancet 2009: 374; 405-15

Wolf H, Frantal S, Pajenda G S, Salameh O, Widhalm H, et al. (2013) Predictive value of neuromarkers supported by a set of clinical criteria in patients with mild traumatic brain injury: S100B protein and neuron-specific enolase on trial: clinical article. J Neurosurg 118: 1298-1303.

Yarnell A M, Shaughness M C, Barry E S, et al. Blast traumatic brain injury in the rat using a blast overpressure model. Current Protocols in Neurosci 2013; 9.41: Supplement 62

Yokobori S, Hosein K, Burks S, Sharma I, Gajavelli S, et al. (2013) Biomarkers for the clinical differential diagnosis in traumatic brain injury—a systematic review. CNS Neurosci Ther 19: 556-565.

You H, Tsutsui S, Hameed S, et al. Aβ neurotoxicity depends on interactions between copper ions, prion protein, and N-methyl-D-aspartate receptors. PNAS 2012; 109(5) 1737-42

Yusa S, Oliveira-Martins J B, Sugita-Konishi Y, Kikuchi Y (2012) Cellular prion protein: from physiology to pathology. Viruses 4: 3109-3131.

Zetterberg H, Smith D H, Blennow K (2013) Biomarkers of mild traumatic brain injury in cerebrospinal fluid and blood. Nat Rev Neurol 9: 201-210.

The invention claimed is:

1. A method of determining and treating a subject that has suffered a traumatic brain injury due to an injury event comprising:
   (i) (a) contacting a blood sample from the subject obtained at a first time point prior to the injury event with a detectable antibody or antibody fragment that binds to cellular prion protein (PrP$^C$);
   (b) quantifying the amount of PrP$^C$ at the first time point indirectly or directly by fluorescence, radioactivity or absorbance;
   (ii) (a) contacting a blood sample from the subject obtained at a second time point after the injury event with a detectable antibody or antibody fragment that binds to PrP$^C$;
   (b) quantifying the amount of PrP$^C$ at the second time point indirectly or directly by fluorescence, radioactivity or absorbance;
   (iii) comparing the amount of PrP$^C$ from the first time point with the amount of PrP$^C$ at the second time point; and
   (iv) selecting a subject with an increased amount of PrP$^C$ at the second time point compared to the first time point in (iii) for undergoing either imaging the brain of the subject by CT scan, treating the subject by surgery, treating the subject with anti-epileptic drugs and/or putting the subject under post-concussion protocol including rest;
   wherein the detectable antibody or antibody fragment is conjugated to an enzyme and the amount of PrP$^C$ is determined by the enzyme activity, is conjugated to biotin and the amount of PrP$^C$ is determined in the presence of streptavidin, or is fluorescently or radioactively labeled and the amount of PrP$^C$ is quantified directly.

2. The method of claim 1, further comprising obtaining a blood sample from the subject prior to contacting the blood sample with the antibody or antibody fragment in (i)(a) and/or (ii)(a).

3. The method of claim 1, wherein the first time point provides a baseline level of the subject and the second time point is following the injury event.

4. The method of claim 3, wherein the subject is an athlete and the baseline level of the subject is from off-season and the second time point is following the injury event.

5. The method of claim 1, wherein the traumatic brain injury is a traumatic brain injury resulting from result of an IED, transportation accident, or sports-related concussion.

6. The method of claim 1, wherein the enzyme is acetylcholinesterase.

7. The method of claim 1, wherein the first time point is prior to combat and the second time point is following a combat-related injury event.

8. A method of detecting PrP$^C$ levels in a subject comprising:
   (i) (a) contacting a blood sample from the subject obtained at a first time point prior to an injury event with a detectable antibody or antibody fragment that binds to cellular prion protein ($PrP^C$);
   (b) quantifying the amount of $PrP^C$ at the first time point indirectly or directly by fluorescence, radioactivity or absorbance;
(ii) (a) contacting a blood sample from the subject obtained at a second time point after the injury event with a detectable antibody or antibody fragment that binds to $PrP^C$; and
   (b) quantifying the amount of $PrP^C$ at the second time point indirectly or directly by fluorescence, radioactivity or absorbance;
wherein the detectable antibody or antibody fragment is conjugated to an enzyme and the amount of $PrP^C$ is determined by the enzyme activity, is conjugated to biotin and the amount of $PrP^C$ is determined in the presence of streptavidin, or is fluorescently or radioactively labeled and the amount of $PrP^C$ is quantified directly.

9. The method of claim 8, further comprising obtaining a blood sample from the subject prior to contacting the blood sample with the antibody or antibody fragment in (i)(a) and/or (ii)(a).

10. The method of claim 8, wherein the enzyme is acetylcholinesterase.

* * * * *